(12) United States Patent
Nampally et al.

(10) Patent No.: US 12,202,840 B2
(45) Date of Patent: Jan. 21, 2025

(54) COMPOUNDS FOR THE TREATMENT OR ALLEVIATION OF DISORDERS ASSOCIATED WITH TAU AGGREGATES

(71) Applicant: AC Immune SA, Lausanne (CH)

(72) Inventors: Sreenivasachary Nampally, Ecublens (CH); Emanuele Gabellieri, Lausanne (CH); Jerome Molette, Prevessin Moens (FR); Heiko Kroth, Ecublens (CH); Cedric Boudou, Reignier (FR)

(73) Assignee: AC Immune SA, Lausanne (CH)

( * ) Notice: Subject to any disclaimer, the term of this patent is extended or adjusted under 35 U.S.C. 154(b) by 1101 days.

(21) Appl. No.: 17/056,270

(22) PCT Filed: May 20, 2019

(86) PCT No.: PCT/EP2019/062940
§ 371 (c)(1),
(2) Date: Nov. 17, 2020

(87) PCT Pub. No.: WO2019/233745
PCT Pub. Date: Dec. 12, 2019

(65) Prior Publication Data
US 2021/0214371 A1    Jul. 15, 2021

(30) Foreign Application Priority Data
Jun. 4, 2018 (EP) .................................. 18175844

(51) Int. Cl.
*C07D 495/14* (2006.01)
*A61K 31/4545* (2006.01)
(Continued)

(52) U.S. Cl.
CPC ........ *C07D 495/14* (2013.01); *A61K 31/4545* (2013.01); *A61K 31/5377* (2013.01);
(Continued)

(58) Field of Classification Search
CPC combination set(s) only.
See application file for complete search history.

(56) References Cited

U.S. PATENT DOCUMENTS

2016/0158242 A1* 6/2016 Kroth ................ A61P 9/00
435/7.1

FOREIGN PATENT DOCUMENTS

| WO | 2010/080253 A1 | 7/2010 |
| WO | 2011/128455 A1 | 10/2011 |
| WO | 2017/009454 A1 | 1/2017 |

OTHER PUBLICATIONS

Goedert M, Eisenberg DS, Crowther RA. Propagation of Tau Aggregates and Neurodegeneration. Annu Rev Neurosci. Jul. 25, 2017;40:189-210. doi: 10.1146/annurev-neuro-072116-031153. PMID: 28772101. (Year: 2017).*

(Continued)

*Primary Examiner* — Jeffrey Stucker
*Assistant Examiner* — Laura Ann Essex
(74) *Attorney, Agent, or Firm* — F. Brent Nix, Esq.; Johnson, Marcou, Isaacs & Nix, LLC

(57) ABSTRACT

The present invention relates to novel compounds that can be employed in the treatment, alleviation or prevention of a group of disorders and abnormalities associated with Tau (Tubulin associated unit) protein aggregates including, but not limited to, Neurofibrillary Tangles (NFTs), such as Alzheimer's disease (AD).

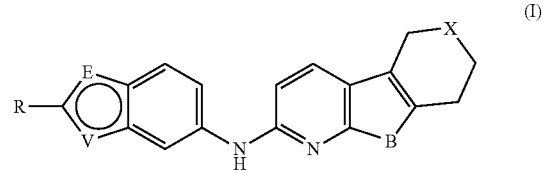

13 Claims, 3 Drawing Sheets

(51) Int. Cl.
*A61K 31/5377* (2006.01)
*A61K 45/06* (2006.01)
*A61P 43/00* (2006.01)
*C07D 471/04* (2006.01)
*C07D 491/048* (2006.01)
*C07D 491/147* (2006.01)
*C07D 495/04* (2006.01)

(52) U.S. Cl.
CPC .............. *A61K 45/06* (2013.01); *A61P 43/00* (2018.01); *C07D 471/04* (2013.01); *C07D 491/048* (2013.01); *C07D 491/147* (2013.01); *C07D 495/04* (2013.01)

(56) References Cited

OTHER PUBLICATIONS

Galvin JE. Prevention of Alzheimer's Disease: Lessons Learned and Applied. J Am Geriatr Soc. Oct. 2017;65(10):2128-2133. doi: 10.1111/jgs.14997. Epub Aug. 2, 2017. PMID: 28766695; PMCID: PMC5937943. (Year: 2017).*

International Searching Authority, International Search Report for PCT/EP2019/062940, Jul. 10, 2019, AC Immune SA.

Written Opinion of the International Searching Authority for PCT/EP2019/062940, Jun. 4, 2018, AC Immune SA.

\* cited by examiner

COMPOUNDS FOR THE TREATMENT OR ALLEVIATION OF DISORDERS ASSOCIATED WITH TAU AGGREGATES

FIELD OF THE INVENTION

The present invention relates to novel compounds that can be employed in the treatment, alleviation or prevention of a group of disorders and abnormalities associated with Tau (Tubulin associated unit) protein aggregates including, but not limited to, Neurofibrillary Tangles (NFTs), such as Alzheimer's disease (AD).

BACKGROUND OF THE INVENTION

Many aging diseases are based on or associated with extracellular or intracellular deposits of amyloid or amyloid-like proteins that contribute to the pathogenesis as well as to the progression of the disease. The best characterized amyloid protein that forms extracellular aggregates is amyloid beta (Aβ). Other examples of amyloid proteins that form extracellular aggregates are prion, ATTR (transthyretin) or ADan (ADanPP). Amyloid-like proteins, that form mainly intracellular aggregates, include, but are not limited to Tau, alpha-synuclein, TAR DNA-binding protein 43 (TDP-43), and huntingtin (htt). Diseases involving Tau aggregates are generally listed as tauopathies such as AD.

Amyloid or amyloid-like deposits result from misfolding of proteins followed by aggregation to give β-sheet assemblies in which multiple peptides or proteins are held together by inter-molecular hydrogen bonds. While amyloid or amyloid-like proteins have different primary amino acid sequences, their deposits often contain many shared molecular constituents, in particular the presence of β-sheet quaternary structures. The association between amyloid deposits and diseases remains largely unclear. A diverse range of protein aggregates, including both those associated and not associated with disease pathologies, have been found to be toxic suggesting that the common molecular features of amyloid are implicated or responsible for disease on-set (Bucciantini et al., Nature, 2002, 416, 507-11). Various multimers of β-sheet aggregated peptides or proteins have also been associated with toxicity for different peptides or proteins ranging from dimers, through to soluble low molecular weight oligomers, protofibrils or insoluble fibrillar deposits.

Alzheimer's disease (AD) is a neurological disorder primarily thought to be caused by amyloid plaques, an extracellular accumulation of abnormal deposit of (amyloid-beta) Aβ aggregates in the brain. The other major neuropathological hallmarks in AD are the intracellular neurofibrillary tangles (NFT) that originate by the aggregation of the hyperphosphorylated Tau protein, misfolded Tau or pathological Tau and its conformers. AD shares its etiopathology with many neurodegenerative tauopathies, in particular with specified types of frontotemporal dementia (FTD). The Tau protein is a freely soluble, "naturally unfolded" protein that binds avidly to microtubuli (MT) to promote their assembly and stability. MT are of major importance for the cytoskeletal integrity of neurons—and thereby for the proper formation and functioning of neuronal circuits, hence for learning and memory. The binding of Tau to MT is controlled by dynamic phosphorylation and de-phosphorylation, as demonstrated mainly in vitro and in non-neuronal cells. In AD brain, Tau pathology (tauopathy) develops later than amyloid pathology, but it is still discussed controversially if Aβ protein is the causative agent in AD which constitutes the essence of the so-called amyloid cascade hypothesis (Hardy et al., Science 1992, 256, 184-185; Musiek et al., Nature Neurosciences 2015, 18(6), 800-806). The exact mechanisms that link amyloid to Tau pathology remain largely unknown, but are proposed to involve activation of neuronal signaling pathways that act on or by GSK3 and cdk5 as the major "Tau-kinases" (Muyllaert et al., Rev. Neurol. (Paris), 2006, 162, 903-7; Muyllaert et al., Genes Brain and Behav. 2008, Suppl 1, 57-66). Even if the tauopathy develops later than amyloid, it is not just an innocent side-effect but a major pathological executer in AD. In experimental mouse models the cognitive defects caused by amyloid pathology are nearly completely alleviated by the absence of Tau protein (Roberson et al., Science, 2007, 316(5825), 750-4) and the severity of cognitive dysfunction and dementia correlates with the tauopathy, not with amyloid pathology.

Diseases involving Tau aggregates are generally listed as tauopathies and they include, but are not limited to, Alzheimer's disease (AD), familial AD, PART (primary age-related Tauopathy), Creutzfeldt-Jacob disease, dementia pugilistica, Down's Syndrome, Gerstmann-Sträussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD, and Huntington's disease. (Williams et al., Intern. Med. J., 2006, 36, 652-60; Kovacs et al., J Neuropathol Exp Neurol. 2008; 67(10): 963-975; Higuchi et al., Neuropsychopharmacology—5th Generation of Progress, 2002, Section 9, Chapter 94: 1339-1354; Hilton et al., Acta Neuropathol. 1995; 90(1):101-6; Iqbal et al., Biochimica et Biophysica Acta 1739 (2005) 198-210; McQuaid et al., Neuropathol Appl Neurobiol. 1994 April; 20(2):103-10; Vossel et al., Lancet Neurol 2017; 16: 311-22; Stephan et al., Molecular Psychiatry (2012) 17, 1056-1076; Anderson et al., Brain (2008), 131, 1736-1748; Savica et al., JAMA Neurol. 2013; 70(7):859-866; Brown et al. Molecular Neurodegeneration 2014, 9:40; El Khoury et al., Front. Cell. Neurosci., 2014, Volume 8, Article 22: 1-18; Tanskanen et al., Ann. Med. 2008; 40(3):232-9; Gupta et al., CAN J OPHTHALMOL—VOL. 43, NO. 1, 2008: 53-60; Dickson et al., Int J Clin Exp Pathol 2010; 3(1):1-23; Fernandez-Nogales et al., Nature Medicine, 20, 881-885 (2014); Bi et al., Nature Communications volume 8, Article number: 473 (2017); Murray et al., Biol Psychiatry. 2014 Apr. 1; 75(7): 542-552).

Of all the agents in clinical trials for the treatment of Alzheimer's disease in 2017, the ones targeting Tau are very scarce and represent only 8% of the Phase II clinical trials (Cummings et al., Alzheimer's & Dementia: Translational Research & Clinical Interventions 3 (2017) 367-384). Current therapeutic approaches that target Tau protein comprise mainly antibody-based approaches with the main limitation of targeting only extracellular Tau. Among the approaches using small molecules, several Tau kinase inhibitors have been developed, despite being very challenging with respect to toxicity and specificity. Nevertheless, currently only one kinase inhibitor, Nilotinib, is tested in clinical trials. Lastly, among the Tau aggregation inhibitors only one, LMTX, is currently in clinical trials (Cummings et al., 2017). Although in recent years, Tau-based treatments have become a point of increasing focus, there is still a big need for additional therapeutic agents that target the pathological Tau conformers that are known or presumed to cause tauopathies.

WO2011/128455 refers to specific compounds which are suitable for treating disorders associated with amyloid proteins or amyloid-like proteins.

WO2010/080253 refers to dipyridyl-pyrrole derivative compounds which are useful in the treatment of diseases amenable to protein kinase signal transduction inhibition, regulation and/or modulation.

SUMMARY OF THE INVENTION

It was an object of the present invention to provide compounds that can be employed in the treatment, alleviation or prevention of a group of disorders and abnormalities associated with Tau protein aggregates including, but not limited to, NFTs, such as Alzheimer's disease (AD). Furthermore, there exists a need in the art for compounds which can be used as therapeutic agents for (a) decreasing Tau aggregates/NFTs by recognizing aggregated Tau and disaggregating Tau, for example by changing the Tau aggregate molecular conformation, and/or (b) preventing the formation of Tau aggregates, and/or (c) interfering intracellularly with Tau aggregates, and/or (d) reducing Tau misfolding and hyperphosphorylation in vivo and/or (f) reducing neuroinflammatory markers. The present inventors have surprisingly found that these objects can be achieved by the compounds of formula (I) as described hereinafter.

The compounds of formula (I) (a) display a high capability in decreasing Tau aggregates by recognizing aggregated Tau and disaggregating Tau, for example by changing the Tau aggregate molecular conformation and/or, (b) prevent the formation of Tau aggregates, and/or (c) interfere intracellularly with Tau aggregates, and/or (d) reduce Tau misfolding and hyperphosphorylation in vivo and/or (f) reduce neuroinflammatory markers. While not wishing to be bound by theory, it is assumed that the compounds of formula (I) inhibit the Tau aggregation or disaggregate preformed Tau aggregates including when present intracellularly. Due to their unique design features, these compounds display properties such as appropriate lipophilicity and molecular weight, brain uptake and pharmacokinetics, cell permeability, solubility and metabolic stability, in order to be a successful medicament for the treatment, alleviation or prevention of tauopathies.

The accumulation of Tau NFT lesions has been shown to correlate well with cognitive deficits in AD, both through histopathological analyses as well as through in vivo Tau PET imaging. The compounds of this invention can either prevent the formation of Tau aggregates, or disaggregate pre-existing Tau aggregates and can therefore be expected to prevent or reduce the associated cognitive deficits in AD.

Ultrastructural analyses have shown that Tau inclusions are composed of paired helical filaments (PHF) or straight filaments (SF). High resolution structural analyses have shown that these filaments are composed of a core region comprising amino acids 306-378 of Tau which adapt a cross beta/beta-helix structure. The compounds of this invention can recognize aggregated Tau and disaggregate Tau, for example by changing the Tau aggregate molecular conformation, and can therefore be expected to facilitate Tau clearance.

In addition, it has been shown that Tau is able to both propagate from cell-to-cell and that certain forms of Tau (acting as seeds) are able to induce the structural change of native Tau protein within the healthy cell to undergo misfolding and aggregation. It is considered that aggregated Tau is responsible for the seeding and thus of the Tau pathology spreading. The compounds of this invention can interfere intracellularly with aggregated Tau and can therefore be expected to reduce Tau pathology spreading and finally prevent or reduce the associated cognitive deficits in AD.

The Tau aggregation cascade initiates with Tau misfolding and hyperphosphorylation. These events are believed to precede the formation of the intracellular Tau neuronal inclusions and therefore the establishment and spreading of the Tau pathology. The compounds of this invention can reduce Tau misfolding and hyperphosphorylation in vivo and can therefore be expected to be beneficial in treating, alleviating, or preventing the diseases associated with Tau pathology.

Lastly, the link between Tau pathology and neuroinflammation is now well established. Neuroinflammation is a key event already in early AD stages and is believed to be one of the causes that trigger aggregation of Tau in PHF. Moreover, several tauopathy mouse models showed significant neuroinflammation once the Tau pathology is well established in the brain indicating that Tau pathology can also induce a neuroinflammatory process. These two findings indicate that Tau pathology and neuroinflammation are linked in a positive feedback loop. The compounds of this invention reduce neuroinflammatory markers in the contest of Tau pathology.

The present invention discloses novel compounds of formula (I) having capabilities to (a) decrease Tau aggregates, recognize aggregated Tau and disaggregate Tau, for example by changing the Tau aggregate molecular conformation and/or, (b) prevent the formation of Tau aggregates, and/or (c) interfere intracellularly with Tau aggregates, and/or (d) reduce Tau misfolding and hyperphosphorylation in vivo and/or (f) reduce neuroinflammatory markers. The present invention provides methods for the treatment of disorders and abnormalities associated with Tau protein aggregates including, but not limited to, NFTs, using a compound of formula (I) or a pharmaceutical composition thereof. The present invention further provides a pharmaceutical composition comprising a compound of formula (I) and a pharmaceutically acceptable carrier or excipient.

The present invention is summarized in the following items:
1. A compound of formula (I):

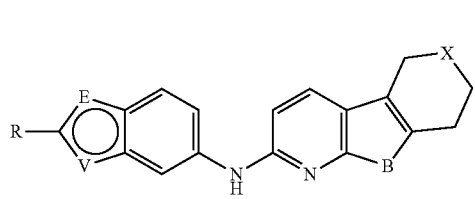

and all stereoisomers, racemic mixtures, tautomers, pharmaceutically acceptable salts, prodrugs, hydrates, solvates and polymorphs thereof;
wherein
B is selected from the group consisting of O and NR$^a$;
E is N and V is S, E is S and V is N, E is N and V is O or E is O and V is N;
X is selected from the group consisting of N—R$^6$ and HC—N(Me)$_2$;
R is independently selected from the group consisting of

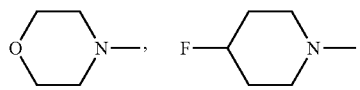

and

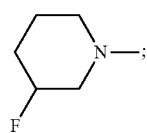

R$^a$ is selected from the group consisting of H and alkyl;
R$^6$ is alkyl;
2. The compound according to item 1, which is a compound of formula (Ia):

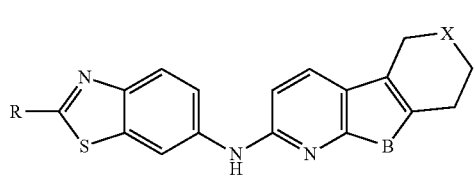

wherein B, R, and X are as defined in item 1.
3. The compound according to item 1, which is a compound of formula (Ib):

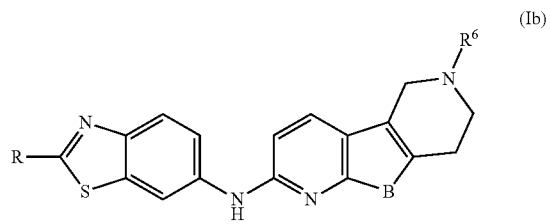

wherein B, R and R$^6$ are as defined in item 1.

4. The compound according to item 1, which is a compound of formula (Ic):

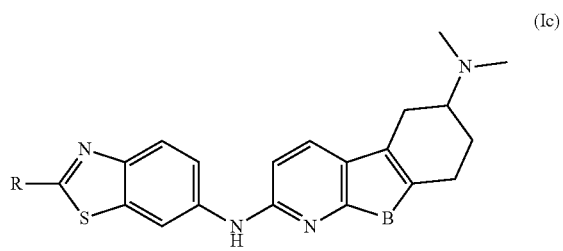

wherein B and R are as defined in item 1.
5. A pharmaceutical composition comprising a compound as defined in any one of items 1 to 4 and optionally a pharmaceutically acceptable carrier or excipient.
6. The compound as defined in any one of items 1 to 4 for use as a medicament.
7. The compound as defined in any one of items 1 to 4 for use in the treatment, alleviation or prevention of a disorder or abnormality associated with Tau protein aggregates.
8. The compound as defined in any one of items 1 to 4 for use in decreasing tau aggregation.
9. The compound as defined in any one of items 1 to 4 for use in preventing the formation of Tau aggregates and/or for use in inhibiting Tau aggregation.
10. The compound as defined in any one of items 1 to 4 for use in interfering intracellularly with Tau aggregates.
11. The compound as defined in any one of items 1 to 4 for use in reducing Tau misfolding and hyperphosphorylation in vivo.
12. The compound as defined in any one of items 1 to 4 for use in reducing neuroinflammatory markers.
13. A method of treating, preventing or alleviating a disorder associated with Tau protein aggregates, the method comprising administering an effective amount of a compound as defined in any one of items 1 to 4 to a subject in need thereof.
14. A method of decreasing tau aggregation, the method comprising administering an effective amount of a compound as defined in any one of items 1 to 4 to a subject in need thereof.
15. A method of preventing the formation of Tau aggregates and/or of inhibiting Tau aggregation, the method comprising administering an effective amount of a compound as defined in any one of items 1 to 4 to a subject in need thereof.
16. A method of interfering intracellularly with Tau aggregates, the method comprising administering an effective amount of a compound as defined in any one of items 1 to 4 to a subject in need thereof.
17. A method of reducing Tau misfolding and hyperphosphorylation in vivo, the method comprising administering an effective amount of a compound as defined in any one of items 1 to 4 to a subject in need thereof.
18. A method of reducing neuroinflammatory markers, the method comprising administering an effective amount of a compound as defined in any one of items 1 to 4 to a subject in need thereof.
19. The use of a compound as defined in any of items 1 to 4 in the manufacture of a medicament for the treatment of a disorder or abnormality associated with Tau protein aggregates.

20. The use of a compound as defined in any of items 1 to 4 in the manufacture of a medicament for decreasing tau aggregation.
21. The use of a compound as defined in any of items 1 to 4 in the manufacture of a medicament for preventing the formation of Tau aggregates and/or for use in inhibiting Tau aggregation.
22. The use of a compound as defined in any of items 1 to 4 in the manufacture of a medicament for interfering intracellularly with Tau aggregates.
23. The use of a compound as defined in any of items 1 to 4 in the manufacture of a medicament for reducing Tau misfolding and hyperphosphorylation in vivo.
24. The use of a compound as defined in any of items 1 to 4 in the manufacture of a medicament for reducing neuroinflammatory markers.
25. A mixture comprising a compound as defined in any one of items 1 to 4 and at least one further biologically active compound selected from a therapeutic agent different from the compound as defined in any one of items 1 to 4, a pharmaceutically acceptable carrier, a diluent and an excipient.
26. The mixture according to item 25, wherein the further biologically active compound is a compound used in the treatment of amyloidosis.
27. The mixture according to item 25 or 26, wherein the further biologically active compound is selected from the group consisting of compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and γ-secretase inhibitors, Tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or Tau modifying drug and nutritive supplements, an antibody, including any functionally equivalent antibody or functional parts thereof or a vaccine.
28. The mixture according to item 27, wherein the further biologically active compound is a cholinesterase inhibitor (ChEI).
29. The mixture according to item 27, wherein the further biologically active compound is selected from the group consisting of tacrine, rivastigmine, donepezil, galantamine, niacin and memantine.
30. The mixture according to item 27, wherein the further biologically active compound is an antibody, particularly a monoclonal antibody, including any functionally equivalent antibody or functional parts thereof.
31. The mixture according to any one of items 25 to 30, wherein the compound and/or the further biologically active compound is/are present in a therapeutically effective amount.
32. The compound for use according to item 7, the method according to item 13, or the use according to item 19, wherein the disorder is selected from Alzheimer's disease (AD), familial AD, Primary Age-Related Tauopathy (PART), Creutzfeldt-Jacob disease, dementia pugilistica, Down's Syndrome, Gerstmann-Sträussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease, preferably Alzheimer's disease (AD), corticobasal degeneration (CBD), Pick's disease (PiD), and progressive supranuclear palsy (PSP).
33. Use of the compound as defined in any of items 1 to 4 as an analytical reference or an in vitro screening tool.

Definitions

Within the meaning of the present application the following definitions apply:

"Alkyl" refers to a saturated straight or branched organic moiety consisting of carbon and hydrogen atoms. Examples of suitable alkyl groups have 1 to 6 carbon atoms, preferably 1 to 4 carbon atoms, and include methyl, ethyl, propyl, isopropyl, n-butyl, t-butyl and isobutyl.

Compounds of the present invention having one or more optically active carbons can exist as racemates and racemic mixtures (including mixtures in all ratios), stereoisomers (including diastereomeric mixtures and individual diastereomers, enantiomeric mixtures and single enantiomers, mixtures of conformers and single conformers), tautomers, atropisomers, and rotamers. All isomeric forms are included in the present invention. Compounds described in this invention containing olefinic double bonds include E and Z geometric isomers. Also included in this invention are all pharmaceutically acceptable salts, prodrugs, polymorphs, hydrates and solvates.

The term "polymorphs" refers to the various crystalline structures of the compounds of the present invention. This may include, but is not limited to, crystal morphologies (and amorphous materials) and all crystal lattice forms. Salts of the present invention can be crystalline and may exist as more than one polymorph.

Solvates, hydrates as well as anhydrous forms of the salt are also encompassed by the invention. The solvent included in the solvates is not particularly limited and can be any pharmaceutically acceptable solvent. Examples include water and $C_{1-4}$ alcohols (such as methanol or ethanol).

"Pharmaceutically acceptable salts" are defined as derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric acid and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts can be found in Remington's Pharmaceutical Sciences, 18$^{th}$ ed., Mack Publishing Company, Easton, Pa., 1990, p. 1445, the disclosure of which is hereby incorporated by reference.

The compounds of the present invention can also be provided in the form of a prodrug, namely a compound which is metabolized in vivo to the active metabolite. As used hereinafter in the description of the invention and in the claims, the term "prodrug" means any covalently bonded compound which releases the active parent pharmaceutical due to in vivo biotransformation. The reference by Goodman and Gilman (The Pharmacological Basis of Therapeutics, 8 ed, McGraw-Hill, Int. Ed. 1992, "Biotransformation of Drugs", p 13-15) describing prodrugs generally is hereby incorporated herein by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The patients or subjects in the present invention are typically animals, particularly mammals, more particularly humans.

"Tau" as used herein refers to a highly soluble microtubule binding protein mostly found in neurons and includes the major 6 isoforms, cleaved or truncated forms, and other modified forms such as arising from phosphorylation, glycosylation, glycation, prolyl isomerization, nitration, acetylation, polyamination, ubiquitination, sumoylation and oxidation.

"Aggregated Tau" refers to aggregated monomers of Tau peptides or proteins which are folded into the oligomeric or polymeric structures.

"Neurofibrillary Tangles" (NFTs) as used herein refer to insoluble aggregates of the hyperphosphorylated Tau protein containing paired helical filaments (PHF) and straight filaments. Their presence is a hallmark of AD and other diseases known as tauopathies.

The definitions and preferred definitions given in the "Definition"-section apply to all of the embodiments described below unless stated otherwise.

DETAILED DESCRIPTION OF THE INVENTION

Figure 1:
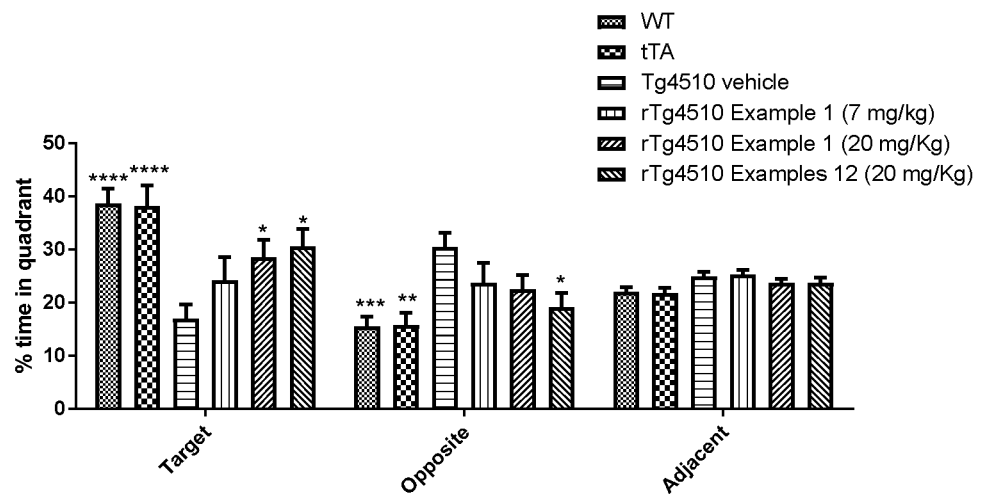
FIG. 1: Morris Water Mazer behavioral test on rTg4510 mice treated with Example 1 and Example 12.

The compounds of the present invention will be described in the following. It is to be understood that all possible combinations of the following definitions are also envisaged.

In one embodiment, the present invention relates to a compound of formula (I):

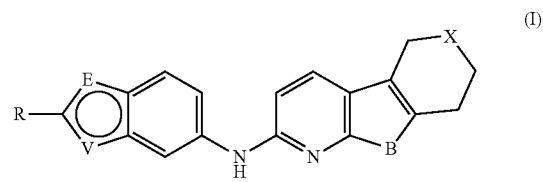

and all stereoisomers, racemic mixtures, tautomers, pharmaceutically acceptable salts, prodrugs, hydrates, solvates and polymorphs thereof.

A preferred embodiment of the compound of formula (I) is

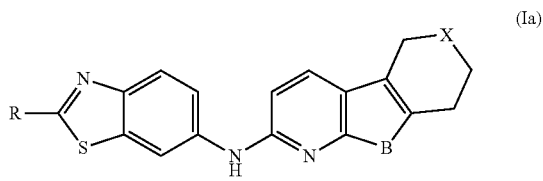

A further preferred embodiment of the compound of formula (I) is

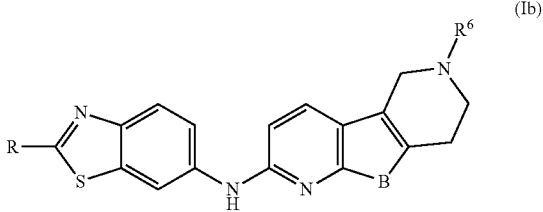

A further preferred embodiment of the compound of formula (I) is

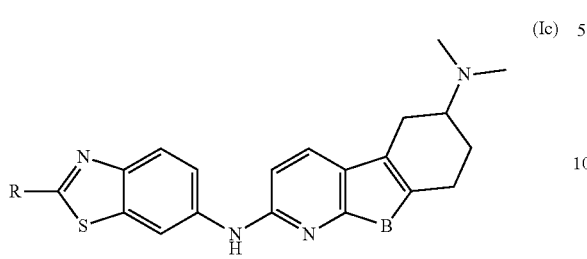

(Ic)

The following definitions apply to the formula (I) and their preferred embodiments, as appropriate.

B is selected from the group consisting of O and NR$^a$. More preferably B is NR$^a$, most preferably NMe.

E is N and V is S, E is S and V is N, E is N and V is O or E is O and V is N. This means that the following groups can be present in the compound of formula (I):

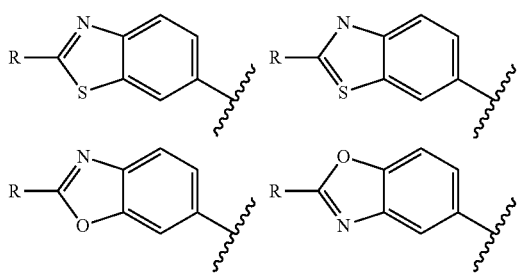

More preferably E is N and V is S or E is N and V is O. Even more preferably E is N and V is S.

X is selected from the group consisting of N—R$^6$ and HC—N(Me)$_2$. In one embodiment, X is N—R$^6$. In another embodiment, X is HC—N(Me)$_2$. In a preferred embodiment, X is

or HC—N(Me)$_2$, even more preferably HC—N(Me)$_2$.

R is independently selected from the group consisting of

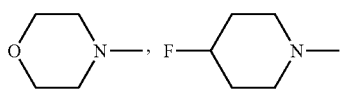

and

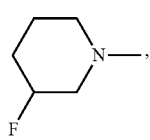

preferably R is

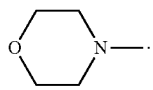

R$^a$ is selected from the group consisting of H and alkyl, more preferably H and Me, even more preferably Me.

R$^6$ is selected from the group consisting of H and alkyl, more preferably alkyl, even more preferably isopropyl.

Preferred compounds are also illustrated in the examples.

Any combination of the embodiments, preferred embodiments and more preferred embodiments disclosed herein is also envisaged in the present invention.

Pharmaceutical Compositions

While it is possible for the compounds of the present invention to be administered alone, it is preferable to formulate them into a pharmaceutical composition in accordance with standard pharmaceutical practice. Thus, the invention also provides a pharmaceutical composition which comprises a therapeutically effective amount of a compound of formula (I) optionally in admixture with a pharmaceutically acceptable carrier, diluent, adjuvant or excipient.

Pharmaceutically acceptable excipients are well known in the pharmaceutical art, and are described, for example, in Remington's Pharmaceutical Sciences, 15$^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-ß-cyclodextrin, polyvinylpyrrolidone, low melting waxes, and ion exchange resins.

The routes for administration (delivery) of the compounds of the invention include, but are not limited to, one or more of: oral (e. g. as a tablet, capsule, or as an ingestible solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e. g. dichlorodifluoromethane, trichlorofluoromethane, dichlorotetra-fluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e. g. using a mixture of ethanol and the propellant as the solvent, which may additionally contain a lubricant, e. g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH was adjusted, sterile saline, or, preferably, as solutions in isotonic, pH was adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

A proposed dose of the compounds according to the present invention for administration to a human (of approximately 70 kg body weight) is 0.1 mg to 1 g, preferably 1 mg to 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may also be used in combination with other therapeutic agents. When a compound of the invention is used in combination with a second therapeutic agent active against the same disease, the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

The pharmaceutical compositions of the invention can be produced in a manner known per se to the skilled person as described, for example, in Remington's Pharmaceutical Sciences, 15$^{th}$ Ed., Mack Publishing Co., New Jersey (1975).

The diseases or conditions that can be treated, alleviated or prevented with the compounds of the present invention are disorders or abnormalities associated with Tau protein aggregates such as neurodegenerative disorders. Examples of diseases and conditions which can be treated, alleviated or prevented are caused by or associated with the formation of neurofibrillary lesions. This is the predominant brain pathology in tauopathy. The diseases and conditions comprise a heterogeneous group of neurodegenerative diseases or conditions including diseases or conditions which show co-existence of Tau and amyloid pathologies.

Examples of the diseases and conditions which can be treated, alleviated or prevented include, but are not limited, to Alzheimer's disease (AD), familial AD, PART (Primary Age-Related Tauopathy), Creutzfeldt-Jacob disease, dementia pugilistica, Down's Syndrome, Gerstmann-Sträussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease. Preferably the diseases and conditions which can be treated, alleviated or prevented include Alzheimer's disease (AD), as well as other neurodegenerative tauopathies such as Creutzfeldt-Jacob disease, dementia pugilistica, amyotrophic lateral sclerosis (ALS), argyrophilic grain disease, corticobasal degeneration (CBD), frontotemporal dementia with Parkinsonism linked to chromosome 17 (FTDP-17), Pick's disease (PiD), progressive supranuclear palsy (PSP), tangle predominant dementia, Parkinson dementia complex of Guam, Hallervorden-Spatz disease, chronic traumatic encephalopathy (CTE), traumatic brain injury (TBI), and other frontotemporal lobar degeneration. More preferably Alzheimer's disease (AD), corticobasal degeneration (CBD), Pick's disease (PiD), and progressive supranuclear palsy (PSP).

The compounds of the present invention can also be employed to decrease protein aggregation, in particular Tau aggregation. The ability of a compound to decrease of Tau aggregation can, for example, be determined using the ThT assay (Hudson et al., FEBS J., 2009, 5960-72).

The compounds of the invention can be used in the treatment of a wide range of disorders in which the neuroinflammation process is associated with misfolding and/or pathologic aggregation of Tau protein.

The compounds of the present invention can be used as an analytical reference or an in vitro screening tool for characterization of tissue with Tau pathology and for testing of compounds targeting Tau pathology on such tissue.

The compounds according to the present invention can also be provided in the form of a mixture with at least one further biologically active compound and/or a pharmaceutically acceptable carrier and/or a diluent and/or an excipient. The compound and/or the further biologically active compound are preferably present in a therapeutically effective amount.

The nature of the further biologically active compound will depend on the intended use of the mixture. The further biologically active substance or compound may exert its biological effect by the same or a similar mechanism as the compound according to the invention or by an unrelated mechanism of action or by a multiplicity of related and/or unrelated mechanisms of action.

Generally, the further biologically active compound may include neutron-transmission enhancers, psychotherapeutic drugs, acetylcholineesterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the further biologically active compound can be selected from the group consisting of a compound used in the treatment of amyloidosis, compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and γ-secretase inhibitors, Tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or Tau modifying drug and nutritive supplements, an antibody, including any functionally equivalent antibody or functional parts thereof, or a vaccine.

In a further embodiment, the mixtures according to the invention may comprise niacin or memantine together with a compound according to the present invention and, optionally, a pharmaceutically acceptable carrier and/or a diluent and/or an excipient.

In still another embodiment of the invention mixtures are provided that comprise as a further biologically active compound "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with a compound according to the invention and, optionally, a pharmaceutically acceptable carrier and/or a diluent and/or an excipient.

Other compounds that can be suitably used in mixtures in combination with the compound according to the present invention are, for example, described in WO 2004/058258 (see especially pages 16 and 17) including therapeutic drug targets (pages 36 to 39), alkanesulfonic acids and alkanolsulfuric acids (pages 39 to 51), cholinesterase inhibitors (pages 51 to 56), NMDA receptor antagonists (pages 56 to 58), estrogens (pages 58 to 59), non-steroidal anti-inflammatory drugs (pages 60 and 61), antioxidants (pages 61 and 62), peroxisome proliferators-activated receptor (PPAR) agonists (pages 63 to 67), cholesterol-lowering agents (pages 68 to 75), amyloid inhibitors (pages 75 to 77), amyloid formation inhibitors (pages 77 to 78), metal chelators (pages 78 and 79), anti-psychotics and anti-depressants (pages 80 to 82), nutritional supplements (pages 83 to 89) and compounds increasing the availability of biologically active substances in the brain (see pages 89 to 93) and prodrugs (pages 93 and 94), which document is incorporated herein by reference.

The invention also includes all suitable isotopic variations of the compounds of the invention. An isotopic variation of the compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, sulphur, fluorine and chlorine such as $^{2}H$, $^{3}H$, $^{13}C$, $^{14}C$, $^{15}N$, $^{17}O$, $^{18}O$, $^{35}S$, $^{18}F$ and $^{36}Cl$ respectively. Certain isotopic variations of the invention, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and delectability. $^{18}F$-labeled compounds are particularly suitable for imaging applications such as PET. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples and Preparations hereafter using appropriate isotopic variations of suitable reagents.

The compounds of the present invention can be synthesized by one of the general methods shown in the following schemes. These methods are only given for illustrative purposes and should not to be construed as limiting.

General Synthetic Schemes for the Preparation of Building Blocks of this Invention:

The compounds of the present invention can be synthesized by one of the general methods shown in the Schemes below. These methods are only given for illustrative purposes and are not limiting.

General Synthetic Scheme for the Preparation of Tricyclic Building Blocks A and A' with X=NCH(CH$_3$)$_2$ and X=CHN(CH$_3$)$_2$.

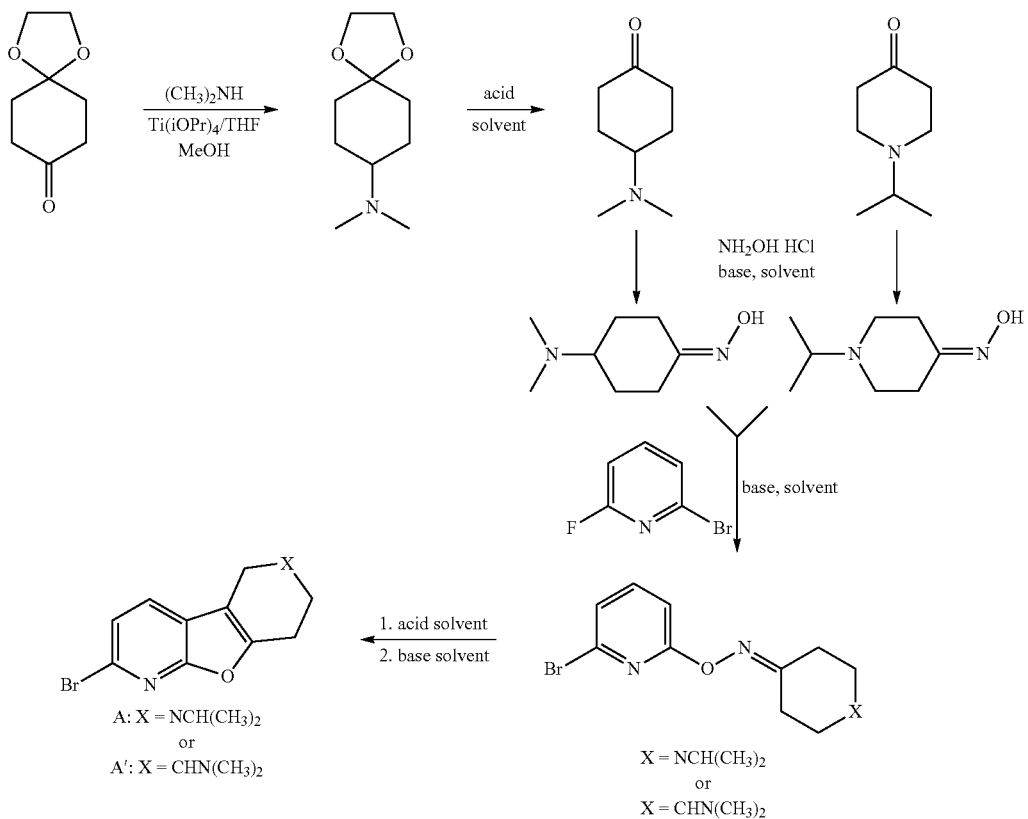

Scheme 1

N,N-dimethyl-1,4-dioxaspiro[4.5]decan-8-amine was prepared by reductive amination of commercially available 1,4-dioxaspiro[4.5]decan-8-one with dimethylamine and obtained after purification. Cleavage of the acetal-group with acid afforded 4-(dimethylamino)cyclohexanone after purification, which was reacted with hydroxylamine to afford 4-(dimethylamino)cyclohexanone oxime after purification. Nucleophilic displacement of the fluoro-atom of 2-bromo-6-fluoropyridine with 4-(dimethylamino)cyclohexanone oxime or commercially available 1-isopropylpiperidin-4-one oxime afforded the O-oxime derivatives with X=CHN(CH$_3$)$_2$ or X=NCH(CH$_3$)$_2$ after purification. Ring closure of the oxime derivative employing Fischer-Indole synthesis conditions afforded the tricyclic building blocks A with X=NCH(CH$_3$)$_2$ or A' with X=CHN(CH$_3$)$_2$ after purification.

General Synthetic Scheme for the Preparation of Tricyclic Building Blocks E, G and H with X=NCH(CH$_3$)$_2$ or CHN(CH$_3$)$_2$ and R$^a$=H or CH$_3$.

with commercially available N,3,3-trimethyl-1,5-dioxaspiro[5.5]undecan-9-amine afforded the tricyclic compound C, which was treated with di-tert-butyl dicarbonate to afford

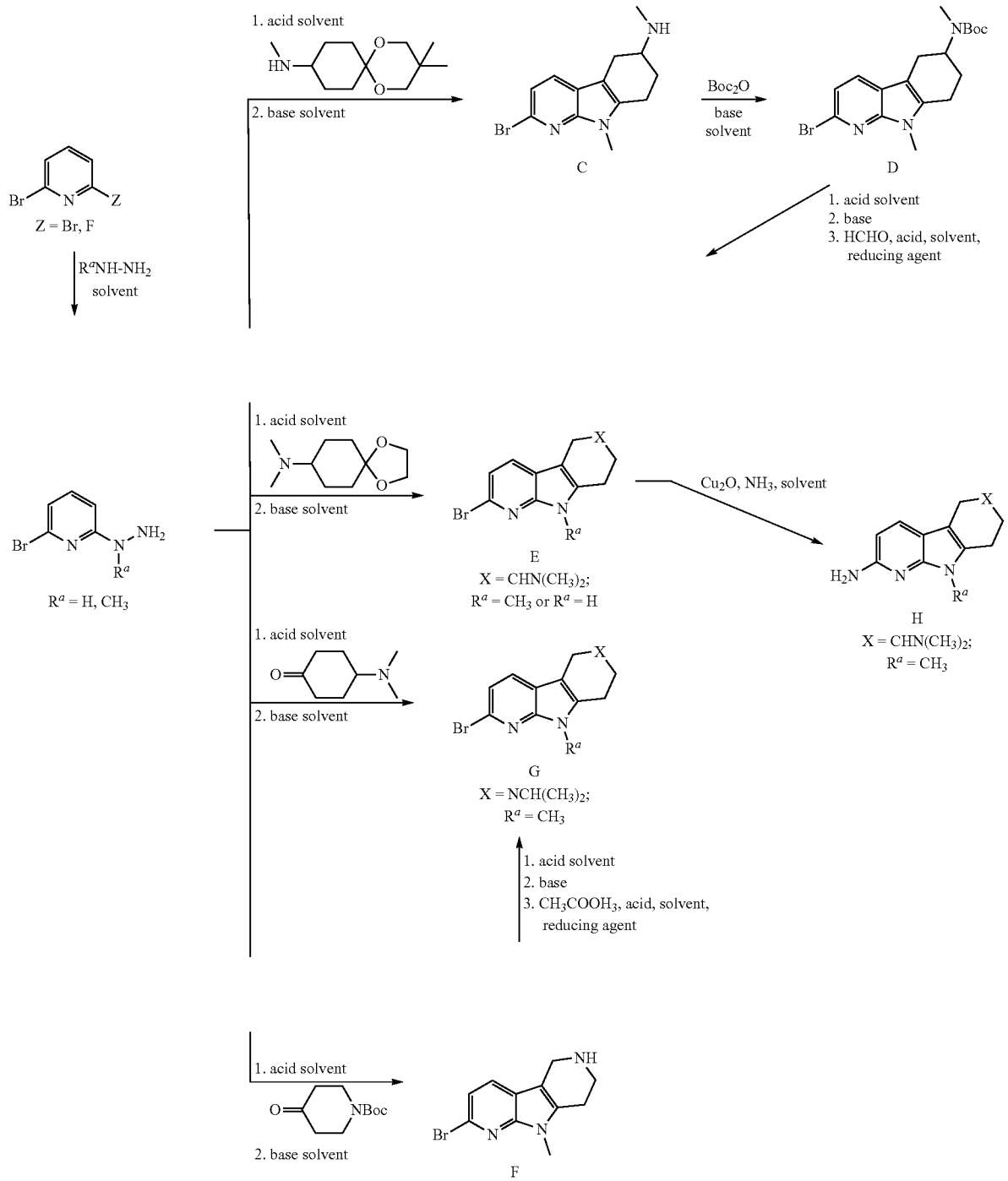

Heating of commercially available 2,6-di-bromopyridine or 2-bromo-6-fluoropyridine with either hydrazine or methylhydrazine in an appropriate solvent afforded the corresponding 2-bromo-6-hydrazino pyridine derivatives (R$^a$=H or CH$_3$) after purification. Fischer-Indole synthesis of the 2-bromo-6-hydrazino pyridine derivatives (R$^a$=H or CH$_3$)

tricyclic compound D after purification. Removal of the Boc-protecting group with acid, followed by reductive amination with formaldehyde afforded tricyclic compound E with X=CHN(CH$_3$)$_2$ and R$^a$=CH$_3$ after purification. Tricyclic compound E with X=CHN(CH$_3$)$_2$ and R$^a$=H or with X=CHN(CH$_3$)$_2$ and R$^a$=CH$_3$ was also prepared via Fischer-Indole synthesis from condensation of the 2-bromo-6-hydrazino pyridine derivatives ($R^a$=H or $CH_3$) with N,N-dimethyl-1,4-dioxaspiro[4.5]decan-8-amine and obtained after purification, Fischer-Indole synthesis of the 2-bromo-6-hydrazino pyridine derivative with $R^a$=$CH_3$ with commercially available tert-butyl 4-oxopiperidine-1-carboxylate afforded the tricyclic compound F after purification. Reductive amination of tricyclic compound F with acetone afforded the tricyclic compound G with X=$NCH(CH_3)_2$ and $R^a$=$CH_3$ after purification. Tricyclic compound G with X=$NCH(CH_3)_2$ and $R^a$=$CH_3$ was also prepared via Fischer-Indole synthesis from condensation of the 2-bromo-6-hydrazino pyridine derivative ($R^a$=$CH_3$) with commercially available 1-isopropylpiperidin-4-one and obtained after purification, Treatment of tricyclic compound E with ammonia and copper(I)-oxide afforded the tricyclic compound H after purification.

General Synthetic Scheme for the Preparation of Benzothiazole and Benzoxazole Building Blocks.

Scheme 3

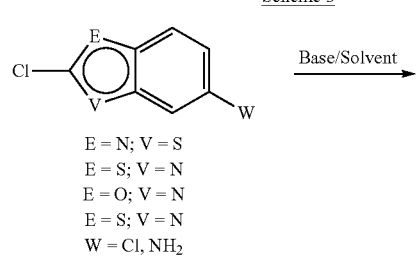

E = N; V = S
E = S; V = N
E = O; V = N
E = S; V = N
W = Cl, $NH_2$

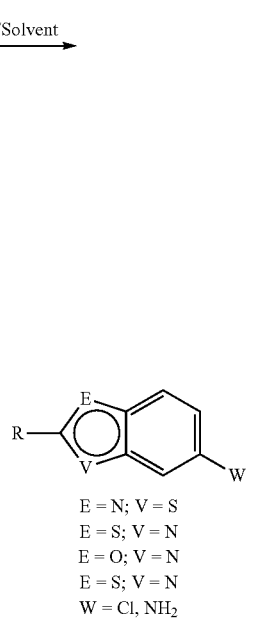

E = N; V = S
E = S; V = N
E = O; V = N
E = S; V = N
W = Cl, $NH_2$

The chloro building blocks (W=Cl or $NH_2$) where E is N and V is S, or E is S and V is N, or E is N and V is O or E is O and V is N, were reacted with commercially available secondary amine building blocks (R=morpholine, 3-fluoropiperidine, 4-fluoropiperidine) by nucleophilic substitution utilizing an appropriate amination protocol in a suitable solvent to afford the desired benzothiazole and benzoxazole building blocks after purification.

General Synthetic Scheme for the Preparation of Compounds of this Invention.

Scheme 4

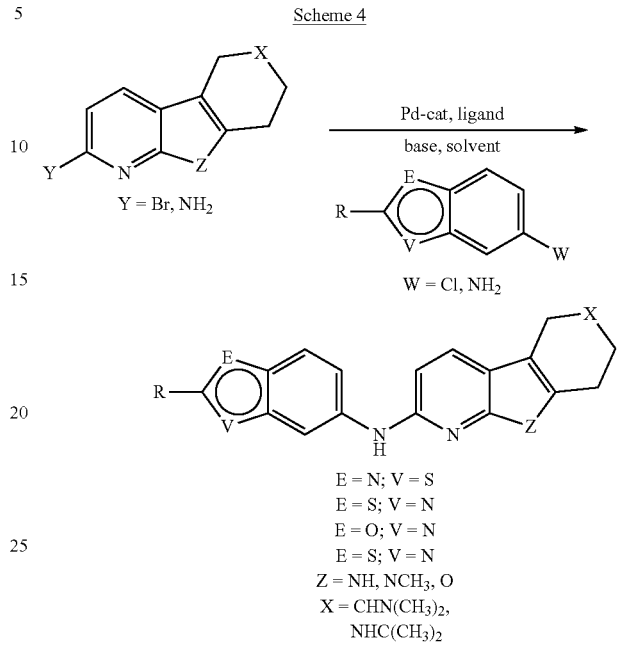

E = N; V = S
E = S; V = N
E = O; V = N
E = S; V = N
Z = NH, $NCH_3$, O
X = $CHN(CH_3)_2$, $NHC(CH_3)_2$

The tricyclic building blocks with Y=Br or $NH_2$ were reacted with benzoxazol or benzothiazol building blocks (W=$NH_2$ or Cl) where E is N and V is S, or E is S and V is N, or E is N and V is O or E is O and V is N), utilizing palladium-coupling chemistry with an appropriate palladium-catalyst and an appropriate ligand in a suitable solvent to afford the desired amination products after purification.

The disaggregation of Tau K18 and full-length (fl) Tau may be measured using any suitable assay known in the art. A standard in vitro assay for measuring the disaggregation capacity is described.

EXAMPLES

All reagents and solvents were obtained from commercial sources and used without further purification. $^1$H-NMR spectra were recorded on Bruker AV 300 and 400 MHz spectrometers in deuterated solvents. Chemical shifts (δ) are reported in parts per million and coupling constants (J values) in hertz. Spin multiplicities are indicated by the following symbols: s (singlet), d (doublet), t (triplet), q (quartet), m (multiplet), bs (broad singlet). Mass spectra were obtained on an Agilent 1290 Infinity II spectrometer with a 6130 Chemstation and an Agilent 1200 Infinity II spectrometer with a 6130 Chemstation. GC-MS data were collected using an Agilent 7890B gas chromatograph and 5977B mass spectrometer. Chromatography was performed using silica gel (Fluka: Silica gel 60, 0.063-0.2 mm) and suitable solvents as indicated in specific examples. Flash purification was conducted with a Biotage Isolera with HP-Sil or KP-NH SNAP cartridges (Biotage) and the solvent gradient indicated in specific examples. Thin layer chromatography (TLC) was carried out on silica gel plates with UV detection.

Preparative Example 1

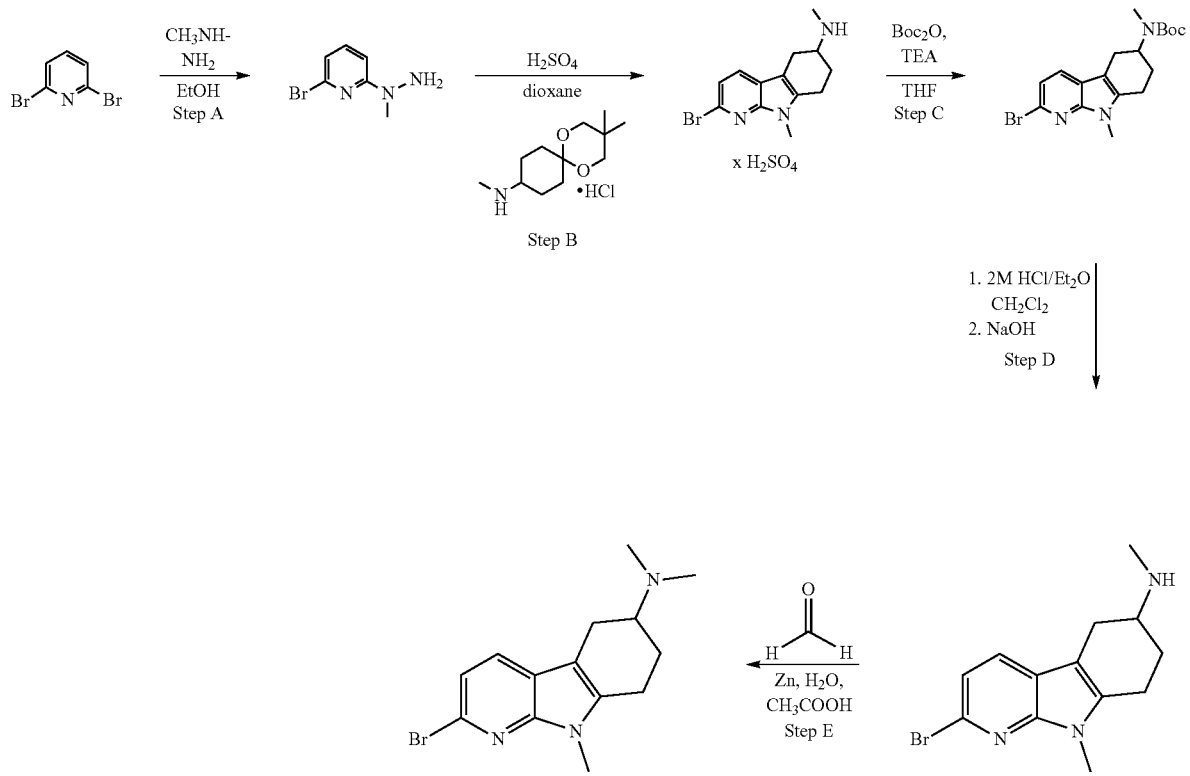

Step A

To a suspension of commercially available 2,6-dibromopyridine (10 g, 42.2 mmol) in ethanol (50 mL) was added commercially available N-methylhydrazine (11.11 mL, 211 mmol). The mixture was heated at 80° C. (reaction mixture temperature) for 48 h. The reaction mixture was concentrated to dryness and the residue purified by chromatography on silica using a Biotage Isolera One purification system employing an ethyl acetate/n-heptane gradient (15/75→35/65) to afford the title compound as reddish oil which becomes a solid by standing at room temperature (7.6 g, 89%).

$^1$H-NMR (400 MHz, CDCl$_3$): δ=7.27 (t, 1H), 6.82 (d, 1H), 6.70 (d, 1H), 4.00 (br-s, 2H), 3.23 (s, 3H)

Step B

A suspension of 4-(methylamino)cyclohexanone-2,2-dimethyltrimethylene ketal hydrochloride (3.7 g, 14.8 mmol) and the title compound from Step A above (3 g, 14.8 mmol) in dioxane (30 mL) was placed in an ice-bath. To the stirred suspension concentrated sulfuric acid (3 mL) was slowly added. After the addition was completed, the reaction mixture was heated at reflux temperature for 5 h using a sand bath (~140° C.). The reaction mixture was cooled to room temperature, the dioxane layer was discarded, and ice-water (20 mL) added. The mixture was stirred until the gummy material was dissolved. Then the pH of the reaction mixture was adjusted to pH=14 using aq. NaOH solution. The aqueous layer was extracted with dichloromethane (200 mL) and the organic phase washed with water and brine. The organic phase was separated, dried over Na$_2$SO$_4$ and the solvent removed under reduced pressure to afford the crude free base (4.7 g). The crude product was directly used in the next step.

Step C

To a solution of the title compound from Step B above (4.7 g) in THF (50 ml) was added triethylamine (5 mL) and di-tert-butyl dicarbonate (10 g, 45.8 mmol). The reaction mixture was stirred at room temperature overnight. Then, the reaction mixture was concentrated and the residue was dissolved in dichloromethane (200 mL). The organic phase was washed with water, brine, dried over Na$_2$SO$_4$ and filtered. The solvent was removed under reduced pressure and the residue purified on a HP-Sil column using a Biotage Isolera One purification system employing an EtOAc/n- heptane gradient (20/80→50/50) to afford the title compound as a white solid (3.55 g, 61% for 2 steps).

¹H-NMR (400 MHz, CDCl₃): δ=) 7.54 (d, 1H), 7.12 (d, 1H), 4.50-4.21 (br-m, 1H), 3.70 (s, 3H), 2.90-2.70 (m, 7H), 2.10-2.00 (m, 2H), 1.46 (s, 9H)

Step D

The title compound from Step C above (1 g, 2.54 mmol) was dissolved in dichloromethane (32 mL) and a 4 M solution of hydrochloric acid in dioxane (16 mL) was added at room temperature. The mixture was stirred at room temperature overnight and the solvents removed under reduced pressure. The residue was suspended in dichloromethane (25 mL) and water (20 mL) and a 1 M aqueous solution of sodium hydroxide added until pH~12. The organic phase was separated and the aqueous phase extracted with dichloromethane (2×20 mL). The combined organic phase was dried over Na₂SO₄, filtered and the solvent removed under reduced pressure to afford the title compound as an off-white solid (0.745 g, 99%).

¹H-NMR (400 MHz, CDCl₃): δ=7.57 (d, 1H), 7.13 (d, 1H), 4.50-4.21 (br-m, 1H), 3.70 (s, 3H), 3.02-2.94 (m, 2H), 2.89-2.81 (m, 1H), 2.79-2.70 (m, 1H), 2.55 (s, 3H), 2.52-2.45 (m, 1H), 2.22-2.15 (m, 1H), 1.88-1.80 (m, 1H)

Step E

The title compound from Step D above (0.745 g, 2.53 mmol) was dissolved in water (2 mL) and acetic acid (0.61 g, 10.12 mmol). Then a 37%-aqueous formaldehyde solution (1.11 g, 13.77 mmol) was added and the mixture was stirred at room temperature for 10 minutes. After the addition of zinc-dust (1.19 g, 18.35 mmol), the reaction mixture was stirred at room temperature for 4 h. Then concentrated aqueous ammonia (10 mL) was added and the mixture was sonicated for 2 minutes. The slurry was extracted with dichloromethane (3×30 mL), the organic phase separated, dried over Na₂SO₄ and the solvent removed under reduced pressure. The residue was purified on a KP-NH column using a Biotage Isolera One purification system employing a dichloromethane/methanol gradient (100/0→90/10) to afford the title compound as a white solid (0.44 g, 56%).

¹H-NMR (400 MHz, CDCl₃): δ=7.60 (d, 1H), 7.16 (d, 1H), 3.72 (s, 3H), 2.97-2.90 (m, 2H), 2.85-2.76 (m, 2H), 2.73-2.63 (m, 1H), 2.48 (s, 6H), 2.35-2.28 (m, 1H), 1.92-1.84 (m, 1H)

Preparative Example 2

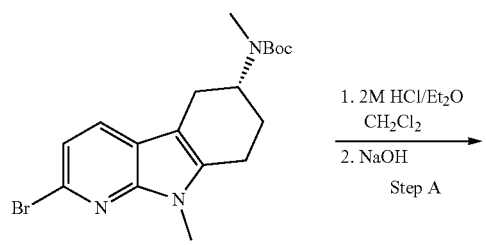

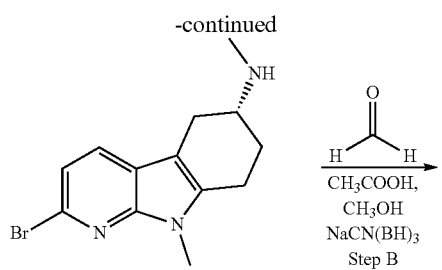

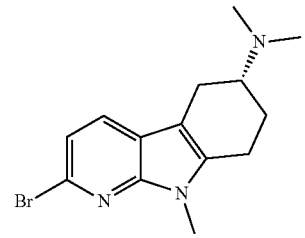

Step A

The chiral starting material (2 g, 5.67 mmol, chemical purity: 99.2%; chiral purity: 99.2% ee), prepared in a similar manner then reported in WO2011/128455 Preparative Example 337, by using DMF rather than MeOH as solvent) was dissolved in dichloromethane (80 mL) and 40 mL of a 4 M solution of hydrogen chloride in 1,4-dioxane was added. The reaction mixture was stirred at room temperature for 18 hours and the solvents removed under reduced pressure. The residue was dissolved in dichloromethane (250 mL) and water (120 mL) and the pH of the aqueous phase was adjusted to pH~12 by adding sodium hydroxide pellets. The organic phase was separated and the aqueous phase extracted with dichloromethane (120 mL). The combined organic phase was dried over Na₂SO₄, filtered and the solvents removed under reduced pressure to afford the title compound as a colorless oil (1.46 g, 98%; TLC matched racemic material).

¹H-NMR (400 MHz, CDCl₃) δ=7.57 (d, 1H), 7.13 (d, 1H), 3.70 (s, 3H), 3.02-2.94 (m, 2H), 2.88-2.70 (m, 3H), 2.56 (s, 3H), 2.53-2.45 (m, 1H), 2.21-2.15 (m, 1H), 1.88-1.80 (m, 1H)

Step B

Compound for Step A above (1.46 g, 4.96 mmol) was suspended in methanol (30 mL) and 37% aqueous formaldehyde solution (3 mL, 35.7 mmol) added. The reaction mixture was stirred at room temperature for 10 minutes and sodium cyanoborohydride (1.25 g, 20.26 mmol) was added. Then acetic acid (4.5 mL) was added (exotherm!) and the reaction mixture was stirred at room temperature for 18 hours. The solvents were removed under reduced pressure and the residue dissolved in dichloromethane (80 mL) and water (40 mL). The pH of the aqueous phase was adjusted to pH~12 by adding sodium hydroxide pellets. The organic phase was separated and the aqueous phase extracted with dichloromethane (40 mL). The combined organic was washed with a mixture of water and brine (40 mL (1/1)), separated, dried over $Na_2SO_4$, filtered and the solvents removed under reduced pressure. The residue was purified by chromatography using a KP-NH-cartridge on a Biotage Isolera system employing a dichloromethane/methanol gradient (100/0→90/10) to afford the title compound as off-white solid (1.36 g, 86%; TLC matched racemic material).

$^1$H-NMR (400 MHz, $CDCl_3$): δ=7.60 (d, 1H), 7.16 (d, 1H), 3.73 (s, 3H), 2.95-2.87 (m, 2H), 2.82-2.63 (m, 3H), 2.44 (s, 6H), 2.29-2.24 (m, 1H), 1.90-1.80 (m, 1H)

Preparative Example 3

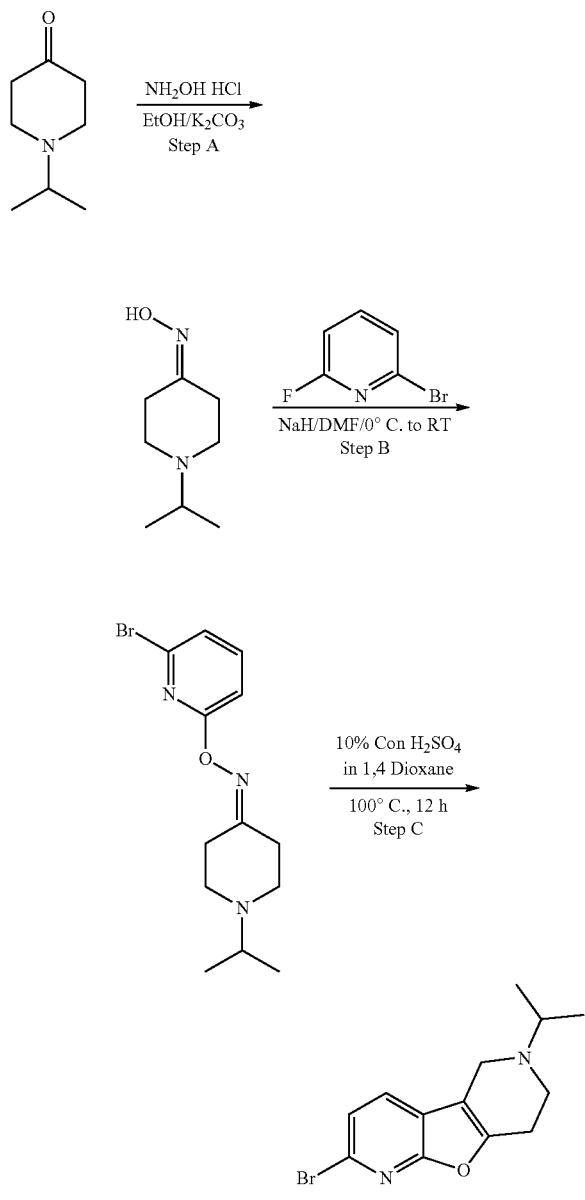

Step A

Commercially available 1-isopropylpiperidin-4-one (500 g, 3.541 mol), hydroxylamine hydrochloride (369.1 g, 5.315 mol) and potassium carbonate (1221 g, 8.855 mol) in ethanol (2.5 L) was heated at 80° C. in an oil bath for 3 h. After completion of the reaction by TLC, the reaction mixture was cooled to 25° C. and the solid was filtered washed with water (5 L) and diethyl ether (2.5 L). The compound was dried under line vacuum for 24 h to get 1-isopropylpiperidin-4-one oxime as a white solid (525 g, 95%)

$^1$H-NMR (400 MHz, DMSO-$d_6$) δ=10.22 (s, 1H), 2.72-2.73 (m, 1H), 2.48-2.50 (m, 4H), 2.43 (s, 2H), 2.17 (t, J=5.68 Hz, 2H), 0.95 (d, J=6.56 Hz, 6H).

MS: 157.2 $(M+H)^+$.

Step B

To a stirred solution of the title compound from Step A above (500 g, 3.201 mol) in DMF (5 L) was added NaH 60% in mineral oil (192 g, 4.801 mol) portionwise at 0° C. After the addition, the reaction mixture was stirred at 25° C. for 1 h and then the reaction mixture was again cooled to 0° C. To this commercially available 2-bromo-6-fluoropyridine (563 g, 3.201 mol) dissolved in DMF (1 L) was added drop wise at 0° C., and the reaction mixture was stirred at 25° C. for 2 h. After completion of the reaction by TLC, the reaction mixture was cooled to 0° C. and quenched with ice water (1 L) followed by extraction using ethyl acetate (10 L). The ethyl acetate layer was washed with water (3×5 L) and brine solution (1×5 L). The organic layer was dried over $Na_2SO_4$, filtered and evaporated to afford the crude product which was purified by column chromatography using 30% to 50% of ethyl acetate in pet ether to afford the title compound as a pale brown liquid (650 g, 65%).

$^1$H-NMR (400 MHz, DMSO-$d_6$) δ=7.76 (t, J=8.00 Hz, 1H), 7.32 (d, J=7.20 Hz, 1H), 7.24 (d, J=8.40 Hz, 1H), 2.80-2.82 (m, 1H), 2.70-2.71 (m, 4H), 2.51-2.57 (m, 2H), 2.40-2.42 (m, 2H), 0.98 (d, J=6.80 Hz, 6H).

MS: 314.1 $(M+2H)^+$.

Step C

To the title compound from Step B above (650 g, 2.08 mol) was added 10% conc. $H_2SO_4$ in 1,4 Dioxane (6.5 L) at 0° C. and then heated to 100° C. for 12 h. After completion of the reaction, the reaction mixture was cooled to 25° C. and the solvent was removed by high vacuum to get the crude material. The crude material was basified by using 30% sodium hydroxide solution followed by extraction using dichloromethane (3×5 L). The dichloromethane layer was washed with brine solution (1×5 L). The organic layer was dried over $Na_2SO_4$, filtered and evaporated to afford the crude product which was purified by column chromatography using 30% to 50% of ethyl acetate in pet ether to afford the title compound as a pale brown liquid (280 g, 45%).

MS: 297.1 $(M+2H)^+$.

Preparative Example 4

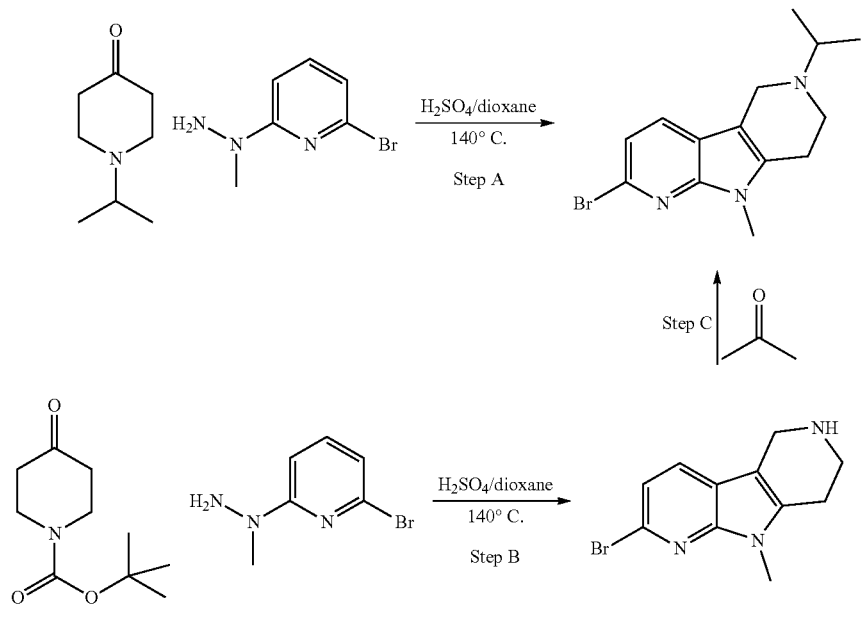

Step A

A suspension of commercially available 1-isopropylpiperidin-4-one (1.56 g, 7 mmol) and 2-bromo-6-(1-methylhydrazinyl)pyridine (2.23 g, 11.0 mmol) in 1,4-dioxane (9 mL) was placed in an ice-bath. To the stirred suspension was added concentrated $H_2SO_4$ (1 mL) slowly. After $H_2SO_4$ addition was completed, the reaction mixture was heated at reflux temperature for overnight using a sand bath (~140° C.). The reaction mixture was cooled to room temperature, and dioxane layer was discarded. The residue was and ice-water (10 mL) added. The mixture was stirred until the gummy material was dissolved. Then the pH of the reaction mixture was adjusted to pH=14 using aq. NaOH solution. The aqueous layer was extracted with DCM (200 mL) and the organic phase washed with water and brine. The organic phase was separated, dried over $Na_2SO_4$ and the solvent removed under reduced pressure to afford the crude free base. The purification was performed on silica gel column using a Biotage Isolera One purification system employing an MeOH/DCM gradient (0/100→20/80) to afford the title compound as solid (0.172 g, 8%).

$^1$H-NMR (400 MHz, $CDCl_3$) δ=7.54 (d, J=8.1 Hz, 1H), 7.14 (d, J=8.1 Hz, 1H), 3.74 (s, 2H), 3.70 (s, 3H), 3.08-3.00 (m, 1H), 2.95 (m, 2H), 2.85 (m, 2H), 1.20 (d, J=6.6 Hz, 6H).

Step B

To a solution of 2-bromo-6-(1-methylhydrazinyl)pyridine (20.00 g, 99 mmol) and tert-butyl 4-oxopiperidine-1-carboxylate (19.72 g, 99 mmol) in 1,4-dioxane (100 ml) was added slowly $H_2SO_4$ (10 ml). The reaction was refluxed for 8 h and was cooled to room temperature and 1N NaOH was added until basic pH. Then, the aqueous phase was extracted with DCM several times. The combined organics were dried over $Na_2SO_4$, filtered and concentrated in vacuo. The oil was triturated in iPrOH and the solid was filtered and dried (3.8 g, 14%).

Step C

To a solution of the title compound from Step B above (1.1 g, 4.13 mmol) and titanium(IV)-isopropoxide (1.453 ml, 4.96 mmol) in acetone (10 ml) was added sodium triacetoxyhydroborate (1.314 g, 6.20 mmol). Then, the reaction was stirred at room temperature for 18 h. 1N NaOH was added and the crude was extracted several times with DCM. The combined organics were dried over $Na_2SO_4$, filtered and concentrated in vacuo. The crude was purified by column chromatography using 2 to 10% MeOH in DCM to afford the title compound as a white solid.

$^1$H-NMR (400 MHz, DMSO-$d_6$) δ=7.75 (d, J=8.1 Hz, 1H), 7.16 (d, J=8.1 Hz, 1H), 3.62 (brs, 5H), 2.98-2.91 (m, 1H), 2.83-2.78 (m, 4H), 1.08 (d, J=6.5 Hz, 1H).

MS: 308.08 $(M+H)^+$.

Preparative Example 5

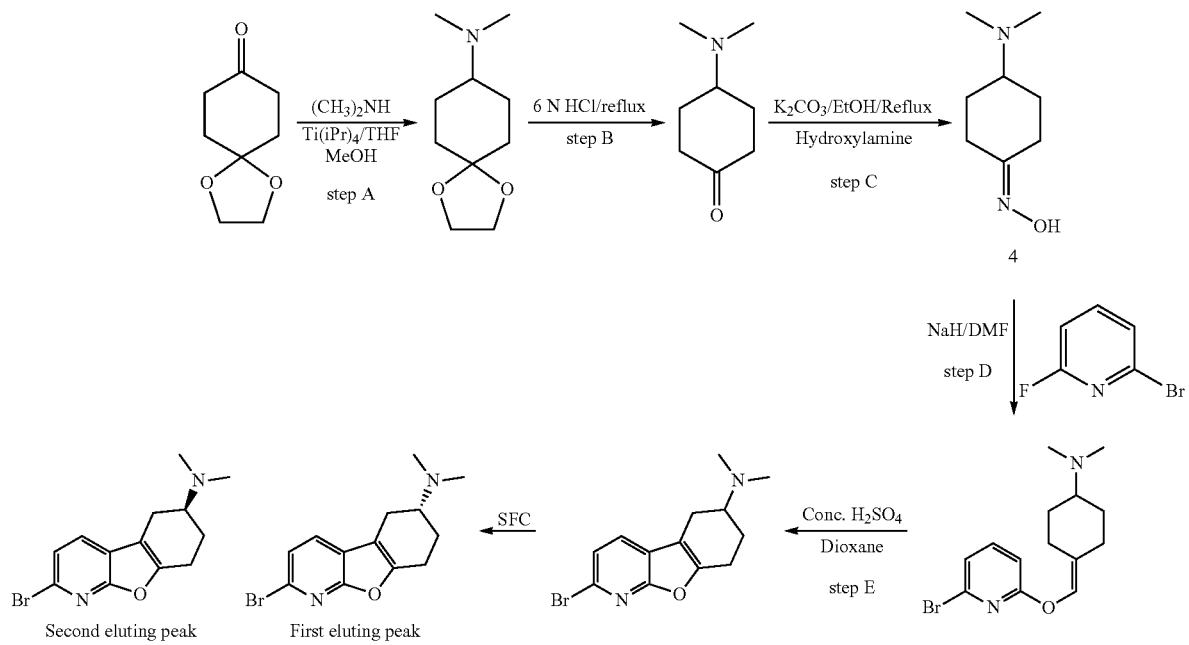

Step A

A suspension of 1,4-dioxaspiro[4.5]decan-8-one (30 g, 192.3 mmol) in THF (30 mL), dimethylamine in THF (195 mL) was slowly added. After the addition reaction mixture was cooled to 0° C., titanium(IV)-propoxide (84 ml, 288.45 mmol) was added drop by drop and stirred room temperature for 4 h. Then reaction mixture was cooled to 0° C. and added methanol (350 ml), sodium borohydride (10.91 g, 288.45 mmol) in a lot manner then stirred for 12 h. After the completion of reaction mixture, water (200 mL) added and stirred well. The solid was filtered and the filtrate was extracted with dichloromethane (200 mL) and the organic phase washed with water and brine. The organic phase was separated, dried over $Na_2SO_4$ and the solvent removed under reduced pressure to afford the title compound as brown liquid that was used directly for the next step (30 g).

MS: 186.2 $(M+H)^+$.

Step B

The title compound from Step A above (20 g, 1 eq) in 6N con. HCl (150 mL) was heated at reflux temperature for 2 h (~100° C.). After the completion of the reaction, the reaction mixture was basified with potassium carbonate (pH=14) and stirred well. The solid was filtered and the filtrate was extracted with dichloromethane (200 mL) and the organic phase washed with brine. The organic phase was separated, dried over $Na_2SO_4$ and the solvent removed under reduced pressure to afford the title compound as brown liquid (12 g, 79%).

MS: 142.2 $(M+H)^+$.

Step C

To a stirred solution of the title compound from Step B above (10.0 g, 70.82 mmol) in ethanol, hydroxylamine hydrochloride (7.38 g, 106.23 mmol) and potassium carbonate (29.3 g, 212.46 mmol) were added and the reaction mixture was heated at 80° C. in an oil bath for 2 h. The reaction mixture was cooled to room temperature and the solvent was removed under reduced pressure. The crude product was diluted with ethyl acetate (150 mL) and water (100 mL). The organic phase was separated, dried over $Na_2SO_4$, filtered and the solvents were removed under reduced pressure to get the crude compound as brown liquid which was directly taken to the next step without further purifications (8.8 g, 72%).

MS: 157 $(M+H)^+$.

Step D

To a stirred solution of the crude title compound from Step C above (8.8 g, 56.4 mmol) in DMF (80 mL) was added NaH (60%) (4.02 g, 112.8 mmol) at 0° C. and stirred for 30 min. Then 2-bromo-6-fluoropyridine (9.9 g, 56.4 mmol) was added and the reaction mixture was stirred at room temperature for 4 h. The crude product was diluted with ethyl acetate (150 mL) and water (100 mL). The organic phase was separated, dried over $Na_2SO_4$, filtered and the solvents were removed under reduced pressure to get the crude compound which was purified on a HP-Sil column using a Biotage Isolera One purification system employing an EtOAc/n-hexane gradient (40/60→50/50) to afford the title compound as a pale yellow solid (8 g, 45%).

1H-NMR, (400 MHz, DMSO-$d_6$) δ=7.76-7.72 (m, 1H), 7.30 (d, J=7.2 Hz, 1H), 7.23 (d, J=8.0 Hz, 1H), 3.31-3.05 (m, 1H), 2.42-2.39 (m, 1H), 2.33-2.27 (m, 3H), 2.26 (s, 6H), 1.93-1.85 (m, 2H), 1.60-1.48 (m, 2H).

MS: 314.3 $(M+H)^+$.

Step E

A suspension of title compound from Step D above (5 g, 24.2 mmol) in 1,4-dioxane (50 mL) was placed in an ice-bath. To the stirred suspension concentrated sulfuric acid (5 mL) was slowly added. After the addition was completed, the reaction mixture was heated at reflux temperature for 12 h (~110° C.). The reaction mixture was cooled to room temperature, the dioxane layer was discarded, and ice-water (20 mL) added. The mixture was stirred until the gummy material was dissolved. Then the pH of the reaction mixture was adjusted to pH=14 using aq. NaHCO$_3$ solution. The aqueous layer was extracted with dichloromethane (200 mL) and the organic phase washed with water and brine. The organic phase was separated, dried over Na$_2$SO$_4$ and the solvent removed under reduced pressure. The purification was performed on silica gel column using a Biotage Isolera One purification system employing a MeOH/DCM gradient (0/100→20/80) to afford title compound as off-white solid (0.150 g, 21%).

$^1$H-NMR, (400 MHz, DMSO-d$_6$) δ=7.97-7.93 (m, 1H), 7.54-7.51 (m, 1H), 2.86-0.77 (m, 4H), 2.31-2.28 (m, 6H), 2.13-2.10 (m, 2H), 1.78 (s, 1H).

MS: 296.9 (M+H)$^+$.

The compound was submitted for SFC separation to afford the pure enantiomers.

SFC Method: FlowRate: 3 ml/min Column Name: Chirapak OX-H

Co-Solvent: 35%. Co-Solvent Name: 0.5% DEA in IPA Injected Volume: 15 μl

Outlet Pressure: 100 bar Temperature: 40° C.

The isomers (0.150 g) were separated by SFC Chiral column to afford first eluting isomer (Rt=3.79) as off white solid 100% enantiomeric purity (0.05 g) and second eluting isomer (Rt=4.63) as off white solid 100% enantiomeric purity (0.04 g).

Preparative Example 6

Step A

To a suspension of commercially available 2,6-dibromopyridine (10 g, 42.2 mmol) in ethanol (50 mL) was added commercially available N-methylhydrazine (11.11 mL, 211 mmol). The mixture was heated at 80° C. (reaction mixture temperature) for 6 h. The reaction mixture was concentrated to dryness and the residue was extracted with dichloromethane (200 mL) and the organic phase washed with water and brine. The organic phase was separated, dried over Na$_2$SO$_4$ and the solvent removed under reduced pressure to as reddish oil which becomes a solid by standing at room temperature (8.2 g, 97%).

MS: 204.2 (M+2H)$^+$.

Step B

A suspension of commercially available 1,4-dioxaspiro[4.5]decan-8-one (30 g, 192.3 mmol) in THF (30 mL), dimethylamine in THF (195 mL) was slowly added. After the addition reaction mixture was cooled to 0° C., Titanium (IV) isopropoxide (84 mL, 288.45 mmol) was added drop by drop and stirred at room temperature for 4 h. Then reaction mixture was cooled to 0° C. and added methanol (350 ml), sodium borohydride (10.91 g, 288.45 mmol) in a lot manner then stirred for 12 h. After the completion of reaction mixture, water (200 mL) was added and stirred well. The solid was filtered and the filtrate was extracted with dichloromethane (200 mL) and the organic phase washed with water and brine. The organic phase was separated, dried over Na$_2$SO$_4$ and the solvent removed under reduced pressure to afford the title compound as brown liquid (30 g, 83%).

MS: 186.2 (M+H)$^+$.

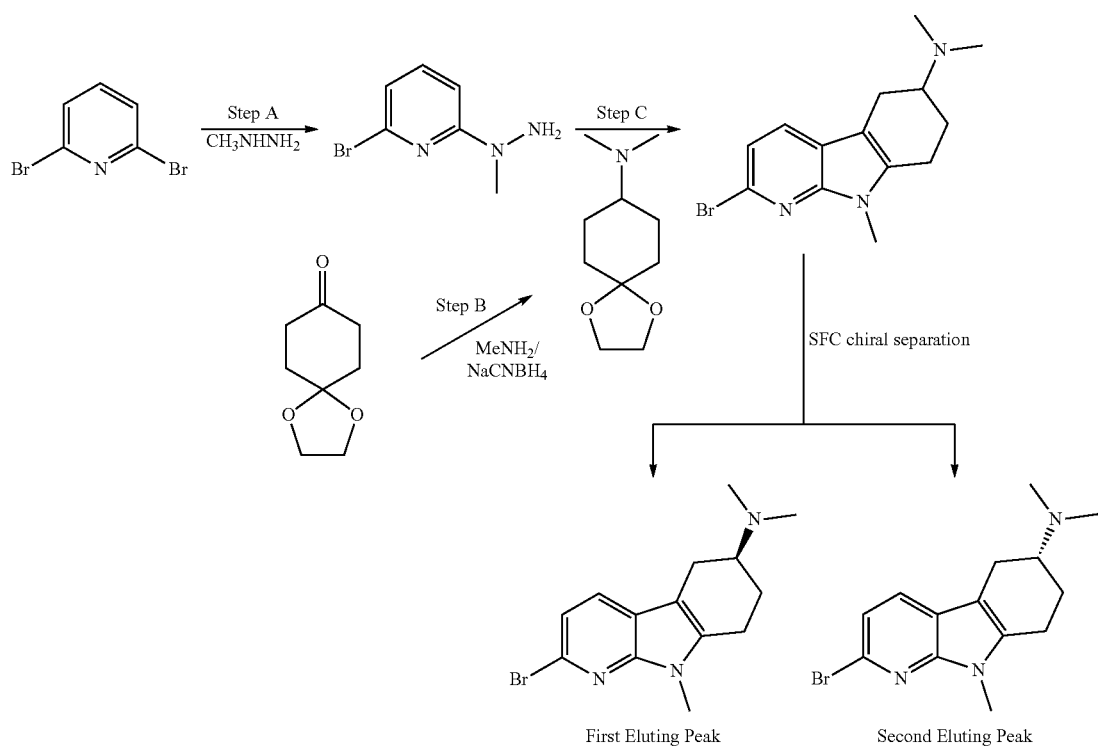

Step C

A suspension of the title compound from Step B above (3.78 g, 27.2 mmol) and the title compound from Step A above (5 g, 24.2 mmol) in 1,4-dioxane (50 mL) was placed in an ice-bath. To the stirred suspension concentrated sulfuric acid (5 mL) was slowly added. After the addition was completed, the reaction mixture was heated at reflux temperature for 12 h (~110° C.). The reaction mixture was cooled to room temperature, the dioxane layer was discarded, and ice-water (20 mL) added. The mixture was stirred until the gummy material was dissolved. Then the pH of the reaction mixture was adjusted to pH=14 using aq. NaHCO$_3$ solution. The aqueous layer was extracted with dichloromethane (200 mL) and the organic phase washed with water and brine. The organic phase was separated, dried over Na$_2$SO$_4$ and the solvent removed under reduced pressure. The purification was performed on silica gel column using a Biotage Isolera One purification System employing MeOH/DCM gradient (0/100→20/80) to afford title compound as brown solid.

MS: 309.2 (M+H)$^+$.

The brown solid was submitted for SFC chiral separation to afford the pure enantiomers.

SFC Method: Column Name: YMC Cellulose C

Co-Solvent: 20 mM Ammonia in Methanol; Co-solvent flow rate: 1.6

Outlet Pressure: 100 bar Temperature: 35° C.

The isomers (2.2 g) were separated by SFC Chiral column to afford first eluting isomer (Rt=3.13) as pale brown solid 100% enantiomeric purity (0.7 g) and second eluting isomer (Rt=4.32) as pale brown solid 100% enantiomeric purity (0.6 g).

Preparative Example 7

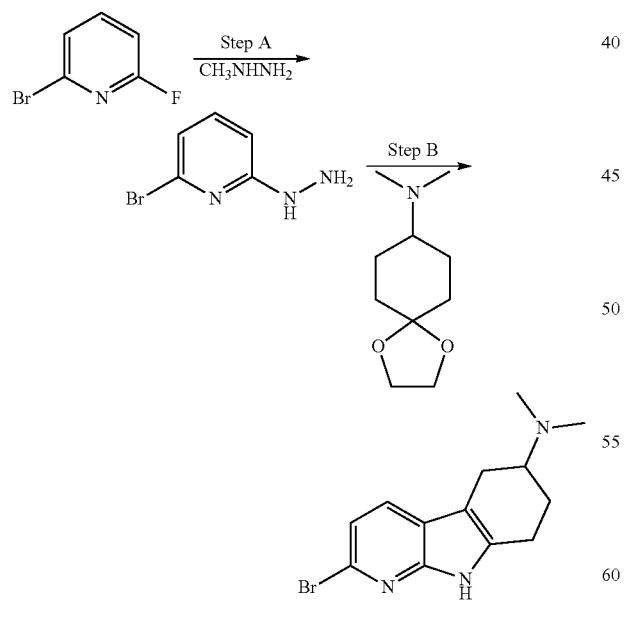

Step A

To a suspension of commercially available 2-bromo-6-fluoropyridine (20 g, 113 mmol) in ethanol (200 mL) was added commercially available N-methylhydrazine (36.6 mL, 568 mmol). The mixture was heated at 115° C. (reaction mixture temperature) for 6 h. The reaction mixture was concentrated to dryness to afford product as off white solid (18 g, 85%).

$^1$H-NMR, (400 MHz, DMSO-d$_6$) δ=7.87 (s, 1H), 7.32-7.36 (m, 1H), 6.64-6.65 (m, 2H).

MS: 189.9 (M+H)$^+$.

Step B

A suspension of the title compound from Preparative Example 6 Step B (2.0 g, 10.79 mmol) and the title compound from Step A above (2.02 g, 10.79 mmol) in 1,4-dioxane (10 mL) was placed in an ice-bath. To the stirred suspension concentrated sulfuric acid (2 mL) was slowly added. After the addition was completed, the reaction mixture was heated in a microwave at 150° C. for 1 hour. The reaction mixture was cooled to room temperature, the dioxane layer was discarded, and ice-water (20 mL) added. The mixture was stirred until the gummy material was dissolved. Then the pH of the reaction mixture was adjusted to pH=14 using aq. NaHCO$_3$ solution. The aqueous layer was extracted with dichloromethane (200 mL) and the organic phase washed with water and brine. The organic phase was separated, dried over Na$_2$SO$_4$ and the solvent removed under reduced pressure. The purification was performed on silica gel column using a Biotage Isolera One purification System employing MeOH/DCM gradient (0/100→20/80) to afford the title compound as brown solid (0.5 g, 16%).

$^1$H-NMR, (400 MHz, DMSO-d$_6$) δ=11.48 (s, 1H), 7.73 (d, J=8.00 Hz, 1H), 7.13 (d, J=8.00 Hz, 1H), 2.67-2.68 (m, 5H), 2.50 (s, 6H), 2.07-2.10 (m, 1H), 1.66-1.68 (m, 1H).

MS: 295.8 (M+H)$^+$.

Preparative Example 8

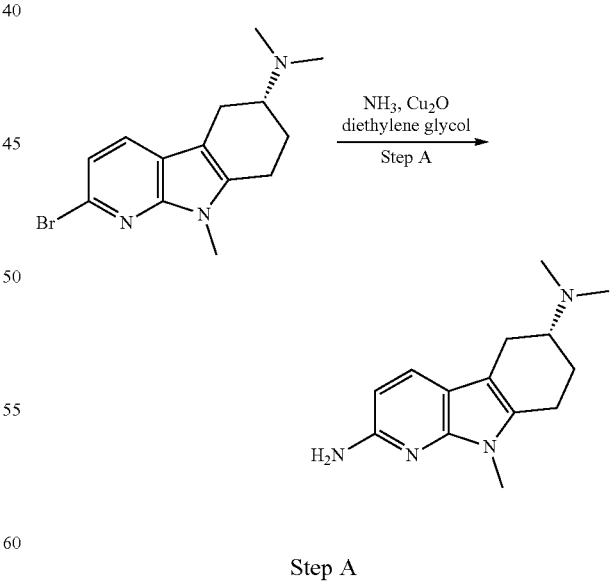

Step A

To a microwave tube were added the tricyclic bromide from the Preparative Example 6 (second eluting peak) (2 g, 6.4 mmol), and 30% NH$_3$ solution (6 mL), Cu$_2$O (0.003 g) and diethylene glycol (1 mL). The tube was sealed and heated at 140° C. for 3 hours using a Biotage Initiator microwave. The reaction mixture was poured in ethyl acetate (200 mL) and washed with water and brine. The organic phase was separated and dried over Na$_2$SO$_4$. The solvent was removed, residue triturated with n-heptane to afford the title compound as off white solid (0.953 g, 61%).

$^1$H-NMR (400 MHz, Chloroform-d) δ=7.54 (d, J=8.2 Hz, 1H), 6.31 (d, J=8.2 Hz, 1H), 4.27 (s, 2H), 3.61 (s, 3H), 2.97-2.80 (m, 2H), 2.79-2.65 (m, 2H), 2.67-2.56 (m, 1H), 2.42 (s, 6H), 2.37-2.18 (m, 1H), 1.95 (d, J=12.8 Hz, 1H), 1.80 (qd, J=11.5, 5.7 Hz, 1H).

Preparative Example 9

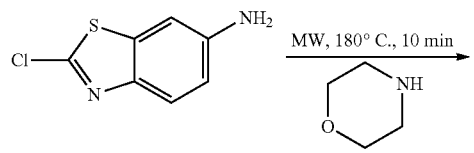

Step A

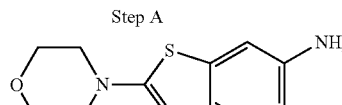

Step A 2-chlorobenzo[d]thiazol-6-amine (950 mg, 5.16 mmol) and morpholine (10 mL) were added in a microwave tube. The tube was sealed and stirred at 180° C. for 10 minutes in a microwave reactor (Biotage). The solvent was removed under reduce pressure and water was added to the crude and triturated at room temperature overnight. The solid was filtered and washed with water (2×10 mL) and dried to afford the title compound as off-white solid (2.00 g, 82%).

$^1$H-NMR (400 MHz, DMSO-d$_6$) δ=7.21 (d, 1H), 6.93 (d, 1H), 6.60 (dd, 1H), 4.94 (s, 2H), 3.72 (t, 4H), 3.43 (t, 5H).

Preparative Example 10

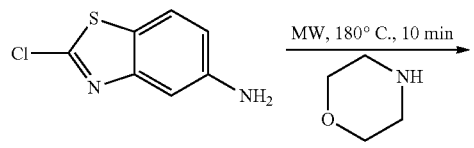

Step A

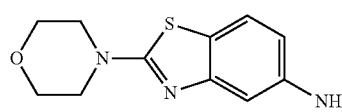

Step A 2-chlorobenzo[d]thiazol-5-amine (400 mg, 2.17 mmol) and morpholine (4 mL) were added in a microwave tube. The tube was sealed and stirred at 180° C. for 10 minutes in a microwave reactor (Biotage). The solvent was removed under reduce pressure and water was added to the crude and triturated at room temperature overnight. The solid was filtered and washed with water (2×10 mL) and dried to afford the title compound as off-white solid (0.38 g, 76%).

$^1$H-NMR (400 MHz, Chloroform-d) δ 7.37=(d, 1H), 6.95 (d, 1H), 6.53 (dd, 1H), 3.91-3.79 (t, 4H), 3.70 (s, 2H), 3.61 (t, 4H).

MS: 236.13 (M+H)$^+$.

Preparative Example 11

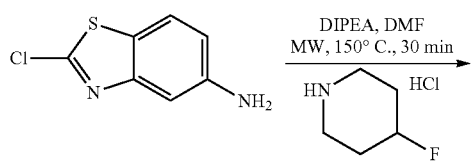

Step A

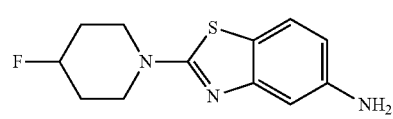

Step A 2-chlorobenzo[d]thiazol-5-amine (250 mg, 1.35 mmol) and 4-fluoropiperidine hydrochloride (419 mg, 3.00 mmol) were added in a microwave tube and DMF (4 mL) followed by DIPEA (0.402 ml, 2.3 mmol) were added. The tube was sealed and stirred at 150° C. for 30 minutes in a microwave reactor (Biotage). The solvent was removed under reduce pressure and the crude was diluted with DCM (15 mL) and saturated solution of ammonium chloride (15 mL). The organic phase was separated and the organic phase was washed with water two more times. The organic phase was dried over Na$_2$SO$_4$, filtered and the solvents were evaporated under reduced pressure. The crude purified twice on HP-Sil column (Biotage), by employing a n-Heptane/EtOAc gradient (100/0→50/50) to afford the title compound (0.25 g, 33%).

$^1$H-NMR (400 MHz, DMSO-d$_6$) δ=7.32 (d, 1H), 6.68 (d, 1H), 6.39 (dd, 1H), 4.99 (s, 2H), 4.87 (tt, 1H), 3.70-3.57 (m, 2H), 3.57-3.43 (m, 2H), 2.08-1.88 (m, 2H), 1.88-1.72 (m, 2H).

Preparative Examples 12 to 13

Following the amination procedure as described in Preparative Example 11, the following compounds were prepared.

TABLE 1

| Preparative Examples | Chloro derivative | Amine | Product Preparative Examples | 1. Yield 2. $^1$H-NMR 3. MH$^+$ (ESI) |
|---|---|---|---|---|
| 12 | H$_2$N-benzothiazole-Cl | HCl, (S)-3-fluoropiperidine | H$_2$N-benzothiazole-N-piperidine-F | 1. 29% 2. $^1$H-NMR (400 MHz, Chloroform-d) δ = 7.35 (d, 1H), 6.94 (s, 1H), 6.51 (d, 1H), 4.94-4.66 (m, 1H), 3.99-3.74 (m, 3H), 3.74-3.59 (m, 3H), 3.59-3.42 (m, 1H), 2.20-1.83 (m, 3H), 1.79-1.48 (m, 1H). 3. 252.22 |
| 13 | H$_2$N-benzothiazole-Cl | HCl, (R)-3-fluoropiperidine | H$_2$N-benzothiazole-N-piperidine-F | 1. 24% 2. $^1$H-NMR (400 MHz, Chloroform-d) δ = 7.36 (d, 1H), 6.95 (d, 1H), 6.52 (dd, 1H), 4.97-4.62 (m, 1H), 3.97-3.74 (m, 2H), 3.74-3.60 (m, 1H), 3.60-3.43 (m, 1H), 2.10-1.86 (m, 3H), 1.80-1.60 (m, 1H). 3. 252.22 |

Preparative Example 14

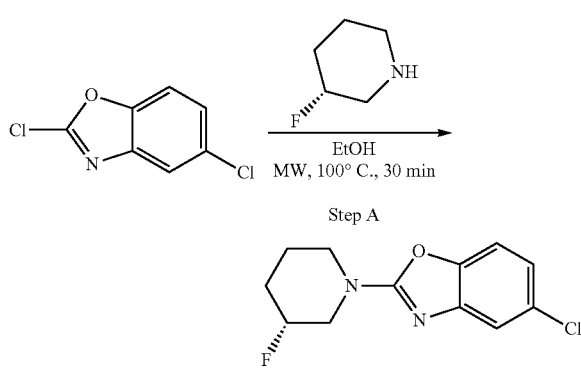

Step A

To a solution of 2,5-dichlorobenzo[d]oxazole (0.35 g, 1.86 mmol) and (R)-3-fluoropiperidine (0.42 g 2.97 mmol) ethanol (12.5 mL) heated reaction mixture using microwave at 100° C. for 60 min. The reaction was cooled to room temperature, dissolved in ethyl acetate (100 mL), and washed with water, brine and dried over Na$_2$SO$_4$. The solvent was removed; the crude product was purified on silica gel column using Biotage purification system with gradient of heptane and ethyl acetate (100/0→80/20) to give title compound (0.225 g, 47%)

$^1$H NMR (400 MHz, Chloroform-d) δ=7.33 (d, J=2.1 Hz, 1H), 7.28 (s, 0H), 7.17 (d, J=8.4 Hz, 1H), 7.00 (dd, J=8.4, 2.1 Hz, 1H), 4.80 (dtt, J=47.1, 5.6, 2.9 Hz, 1H), 4.04 (dddt, J=13.9, 9.5, 5.4, 1.2 Hz, 1H), 3.97-3.86 (m, 1H), 3.80-3.64 (m, 1H), 3.51 (dddd, J=13.5, 9.0, 3.4, 1.8 Hz, 1H), 2.13-1.96 (m, 2H), 1.69 (tdd, J=11.3, 5.5, 3.3 Hz, 2H).

Preparative Example 15

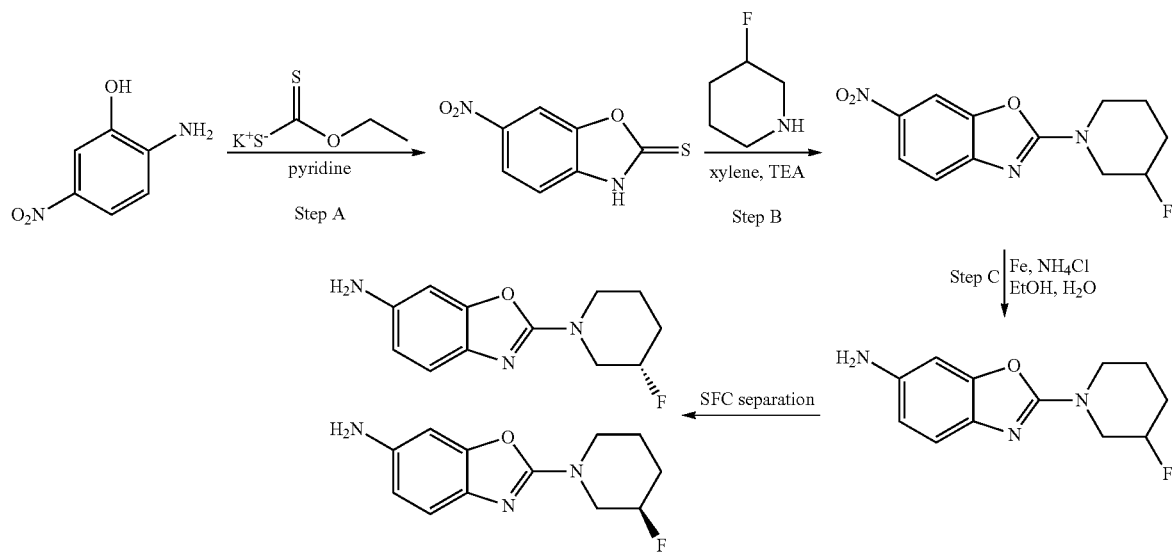

Step A 2-amino nitrophenol (1 g, 6.48 mmol) was taken in pyridine, added potassium ethyl xanthate (1.14 g, 7.13 mmol). The mixture was heated at 120° C. for 8 h. After the completion of reaction, the mixture was acidified with 1.5N HCl. The solid obtained was collected by filtration and dried under vacuum to afford the title compound as yellow solid (1 g, 78%).

MS: 197.18 $(M+H)^+$.

Step B

To a solution of the title compound from Step A above (1 g, 5.09 mmol) in xylene (10 mL), added triethylamine (2.14 mL, 15.29 mmol) and 3-fluoropiperidine (0.52 g, 5.09 mmol). The resulting mixture was heated at 100° C. for 16 h. After the completion of reaction, the mixture was evaporated, to the residue was dissolved in ethyl acetate and washed with water. The organic layer was dried over anhydrous $Na_2SO_4$ and evaporated to get the crude, which was purified by flash chromatography using 40-50% ethylacetate in petroleum ether to afford the title compound as light brown solid (1.1 g, 81%).

$^1$H-NMR (400 MHz, DMSO-$d_6$) δ=8.06 (s, 1H), 7.96-7.97 (m, 1H), 7.63 (d, J=8.80 Hz, 1H), 4.86-4.86 (m, 1H), 4.07-4.09 (m, 1H), 3.96-3.97 (m, 1H), 3.60-3.63 (m, 1H), 3.38-3.39 (m, 1H), 2.49-2.50 (m, 1H), 1.91-1.92 (m, 2H), 1.80-1.81 (m, 2H), 1.61-1.62 (m, 1H), MS: 266.0 $(M+H)^+$.

Step C

To a solution of the title compound from Step b above (1.1 g, 4.15 mmol) in ethanol and water (2:1 ratio) was added iron power (1.14 g, 20.75 mmol) and ammonium chloride (2.19 g, 41.5 mmol). The resulting suspension was heated at 90° C. for 2 h. After the completion reaction the mixture was filtered through celite, the filtrate was evaporated and the crude was purified by flash chromatography to get 2-(3-fluoropiperidin-1-yl)-2,3-dihydrobenzo[d]oxazol-6-amine. (0.2 g, 20%).

MS: 236.2 $(M+H)^+$.

Two isomers were separated by chiral separation. to get each enantiomer.

Method: mobile phase: 0.1% DEA in n-HEXANE:ETOH: 60:40

COLUMN: CHIRALCEL OJ-H (250×4.6) mm, 5 μm.

The isomers (0.2 g) were separated by Chiral column to afford first eluting isomer (Rt=14.2) as off white solid 100% enantiomeric purity (0.04 g) and second eluting isomer (Rt=21.7) as off white solid 100% enantiomeric purity (0.04 g).

Example 1

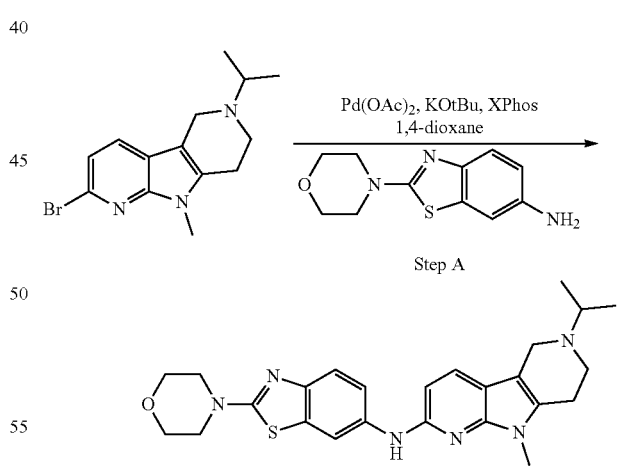

Step A 1,4-Dioxane (4 mL) was degassed for 10 minutes with argon. Palladium(II)-acetate (0.0675 g, 0.301 mmol) and dicyclohexyl(2',4',6'-triisopropyl-[1,1'-biphenyl]-2-yl)phosphine (XPhos, 0.43 g, 0.902 mmol) were added. The suspension was then heated at 110° C. for 2 minutes. Then the title compound from Preparative Example 4 (0.927 mg, 3.01 mmol), the title compound from Preparative Example 9

(0.849 g, 3.61 mmol) and sodium tert-butoxide (0.867 g, 9.02 mmol) were added and the reaction mixture was stirred at 110° C. for 2 hours. The reaction was cooled to room temperature and concentrated to dryness. 1 N NaOH was added and the aqueous phase was extracted with dichloromethane/methanol several times. The combined organics were dried over $Na_2SO_4$, filtered and concentrated in vacuo. The crude material was purified twice by column chromatography using 2 to 10% methanol in dichloromethane. The solid obtained was triturated in methanol/isopropanol, filtered and dried to afford the title compound as a white solid (0.6339 g, 46%).

$^1$H-NMR (400 MHz, DMSO-$d_6$) δ=8.89 (brs, 1H), 8.49 (brs, 1H), 7.58 (d, J=8.3 Hz, 1H), 7.49 (dd, J=8.7, 1.7 Hz, 1H), 7.39 (d, J=8.7 Hz, 1H), 6.53 (d, J=8.3 Hz, 1H), 3.74-3.72 (m, 4H), 3.61 (brs, 5H), 3.50-3.48 (m, 4H), 2.96-2.75 (m, 5H), 1.10 (d, J=5.7 Hz, 6H).

MS: 463.37 $(M+H)^+$.

Example 2

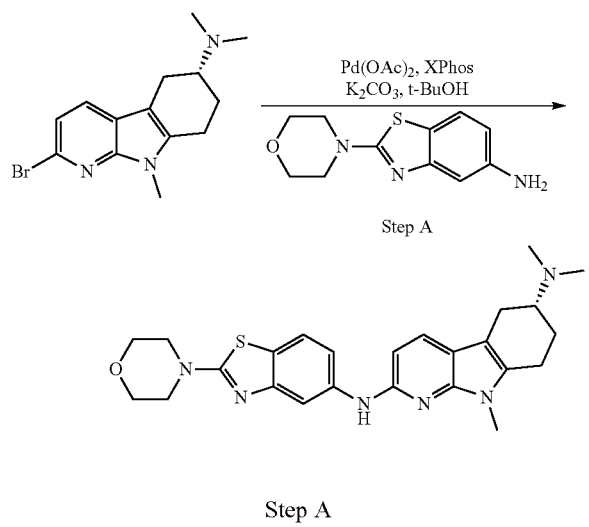

Step A

An oven dried schlenk flask evacuated and back filled with Argon gas. Then 2-dicyclohexylphosphino-2',4',6'-triisopropylbiphenyl (XPhos, 0.046 g, 0.10 mmol) and palladium(II) acetate (0.007 g, 0.03 mmol) were added followed by dry 1,4-dioxane (8 mL) and heated at 110° C. in a sand-bath for 90 seconds to generate the catalyst (clear red solution). The title compound from Preparative Example 6 second eluting peak (0.100 g, 0.32 mmol), the title compound from Preparative Example 10 (0.091 g, 0.39 mmol) and sodium tert-butoxide (0.102 g, 1.07 mmol) were added. The mixture was heated in a sand-bath at ~110° C. for 4 h. The mixture was diluted with dichloromethane (200 mL) and washed with water (100 mL) and brine solution (100 mL). The organic phase was dried over $Na_2SO_4$, filtered and the solvents removed. The residue was purified on a HP-SIL cartridge using a Biotage Isolera One purification system employing a dichloromethane/methanol gradient (100/0→80/20). The collected compound precipitate was triturated with ethyl acetate and heptane mixture (2:8) and the solid was dried to afford the title compound as white solid (0.085 g, 57%).

$^1$H-NMR (400 MHz, DMSO-$d_6$): δ=8.86 (s, 1H), 8.48 (d, 1H), 7.58 (d, 1H), 7.47 (dd, 1H), 7.39 (d, 1H), 6.52 (d, 1H), 3.76-3.70 (m, 4H), 3.60 (s, 3H), 3.51-3.46 (m, 4H), 2.88-2.55 (m, 5H), 2.46-2.43 (m, 1H), 2.26 (s, 6H), 2.12-2.06 (m, 1H), 1.70-1.60 (m, 1H)

Example 3

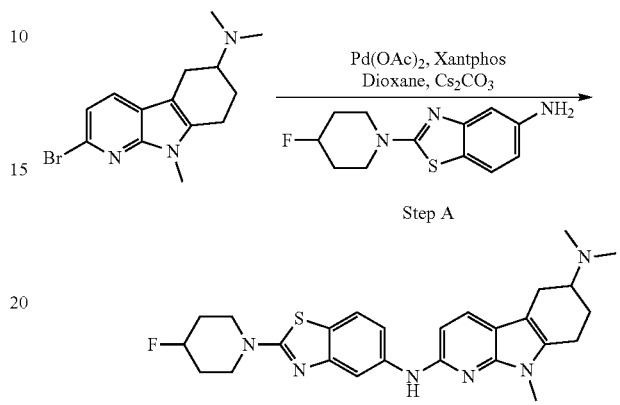

Step A

Palladium(II) acetate (0.00583 g, 0.026 mmol) and 4,5-bis(diphenylphosphino)-9,9-dimethylxanthene (XantPhos, (0.0451 g, 0.078 mmol) were added to a reaction vial and degassed 1,4-dioxane (4 ml) was added. The vial was filled with argon gas and sealed. The suspension was heated at 110° C. for 1 minute and the title compound from Preparative Example 6 (0.08 g, 0.260 mmol), the title compound from Preparative Example 11 (0.078 g, 0.311 mmol) and cesium carbonate (0.254 g, 0.779 mmol) were added and the solution was heated at 110° C. for 4 hours. The reaction mixture was diluted with ethyl acetate (10 mL) and water (10 mL). The organic phase was separated and the aqueous phase was extracted with ethyl acetate two more times. The combined organic phase was dried over $Na_2SO_4$, filtered and the solvents were evaporated under reduced pressure. The crude purified on HP-Sil column (Biotage), by employing a DCM/MeOH gradient (100/0→80/20) to afford the title compound (0.071 g, 57%).

$^1$H-NMR (400 MHz, DMSO-$d_6$) δ=8.86 (s, 1H), 8.05 (d, 1H), 7.64-7.54 (m, 2H), 7.45 (dd, 1H), 6.57 (d, 1H), 4.95 (ddt, 1H), 3.75-3.52 (m, 9H), 2.90-2.56 (m, 4H), 2.30 (s, 6H), 2.17-1.92 (m, 2H), 1.83 (ddq, 2H), 1.68 (qd, 1H).

MS: 479.14 $(M+H)^+$.

Example 4

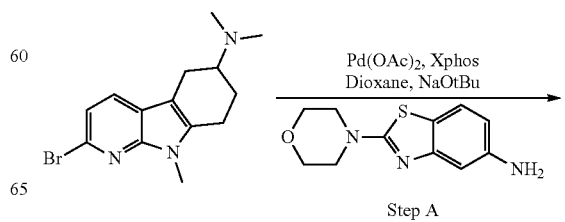

Step A

-continued

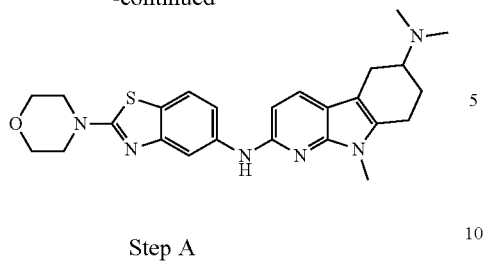

Step A

Palladium(II) acetate diacetoxypalladium (0.0038 g, 0.017 mmol) and dicyclohexyl(2',4',6'-triisopropyl-[1,1'-biphenyl]-2-yl)phosphine (XPhos, 0.024 mg, 0.050 mmol) were added to a reaction vial and degassed 1,4-dioxane (4 ml) was added. The vial was filled with Argon gas and sealed. The suspension was heated at 110° C. for 1 minute and the title compound from Preparative Example 4 (0.050 g, 0.16 mmol), the title compound from Preparative Example 10 (0.0485 g, 0.20 mmol) and sodium tert.-butoxide (0.0540 g, 0.56 mmol) were added and the solution was heated at 110 C for 3 hours. The reaction mixture was diluted with ethyl acetate (5 mL) and water (5 mL). The organic phase was separated and the aqueous phase was extracted with ethyl acetate two more times. The combined organic phase was dried over $Na_2SO_4$, filtered and the solvents were evaporated under reduced pressure. The residue was purified on HP-Sil SNAP cartridges using a Biotage Isolera One purification system employing a DCM/MeOH (9:1) to afford the title compound (0.016 g, 22%).

$^1$H-NMR (400 MHz, DMSO-$d_6$) δ=8.88 (s, 1H), 8.08 (d, 1H), 7.59 (d, 2H), 7.45 (dd, 1H), 6.56 (d, 1H), 3.73 (dd, 4H), 3.62 (s, 5H), 3.56-3.46 (m, 4H), 3.04-2.88 (m, 1H), 2.84 (s, 2H), 2.75 (s, 2H), 1.09 (d, 6H).

MS: 463.20 (M+H)$^+$.

Example 5

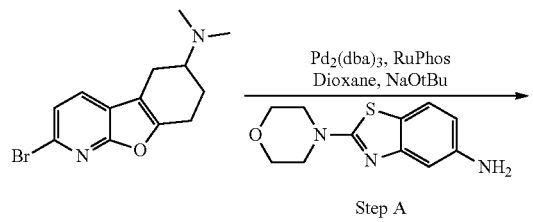

Step A

-continued

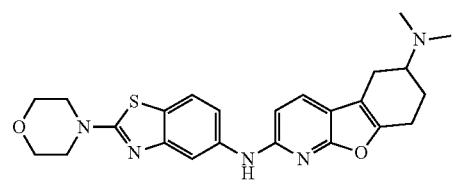

Step A

To a stirred solution of the title compound from Preparative Example 5 (0.10 g, 0.33 mmol) and the title compound from Preparative Example 10 (0.063 g, 0.27 mmol) in 1,4-dioxane (5 mL) was degassed with nitrogen for 15 min. Then sodium tert-butoxide (0.086 g, 0.99 mmol), 2-dicyclohexylphosphino-2',6'-diisopropoxybiphenyl (RuPhos, (0.016 g, 0.033 mmol) and tris(dibenzylideneacetone)dipalladium(0) ($Pd_2(dba)_3$, 0.015 g, 0.002 mmol) was added and heated to 100° C. for 6 h. After completion of the reaction by TLC, the reaction mixture was filtered through celite washed with methanol and DCM, the filtrate was concentrated. The crude product was purified by silica column, using 8-10% MeOH in DCM to afford the title compound as off-white solid (0.015 g, 10%).

$^1$H-NMR (400 MHz, DMSO-$d_6$) δ=9.18 (bs, 1H), 8.12 (d, J=1.60 Hz, 1H), 7.73 (d, J=8.40 Hz, 1H), 7.62 (d, J=8.40 Hz, 1H), 7.25 (dd, J=1.60, 8.60 Hz, 1H), 6.76 (d, J=8.40 Hz, 1H), 3.72-3.73 (m, 4H), 3.54-3.55 (m, 4H), 2.67-2.77 (m, 5H), 2.28 (s, 6H), 2.06-2.09 (m, 1H), 1.73-1.75 (m, 1H).

MS: 450.2 (M+H)$^+$.

Examples 6 to 36

Following the palladium coupling procedures as described in Preparative Examples 1, 2, 3, 4 and 5 the following compounds were prepared.

TABLE 2
| Examples | Halogen derivative | Amine | Product Examples | 1. Yield  2. ¹H-NMR  3. MH⁺ (ESI)  4. Synthesis procedure |
|---|---|---|---|---|
| 6 | | | | 1. 47%  2. ¹H-NMR (400 MHz, DMSO-$d_6$) δ = 8.87 (s, 1H), 8.03 (d, 1H), 7.64-7.51 (m, 2H), 7.45 (dd, 1H), 6.57 (d, 1H), 4.94 (ddt, 1H), 3.77-3.47 (m, 9H), 3.09-2.64 (m, 5H), 2.14-1.92 (m, 2H), 1.88-1.69 (m, 2H), 1.11 (d, 6H).  3. 479.50  4. Example 3 |
| 7 | | | | 1. 10%  2. ¹H-NMR (400 MHz, DMSO-$d_6$) δ = 9.20 (bs, 1H), 8.33 (d, J = 1.20 Hz, 1H), 7.71 (d, J = 8.00 Hz, 1H), 7.39-7.44 (m, 2H), 6.74 (d, J = 8.40 Hz, 1H), 3.73-3.75 (m, 4H), 3.50-3.55 (m, 6H), 2.94-3.00 (m, 1H), 2.74-2.84 (m, 4H), 1.09 (d, J = 6.80 Hz, 6H).  3. 450.2  4. Example 5 |
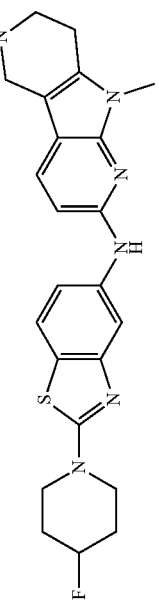
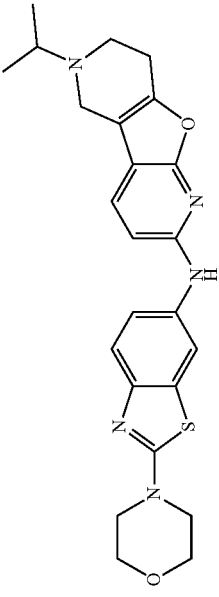

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 8 | | | | 1. 18%;<br>2. ¹H-NMR (400 MHz, DMSO-d₆) δ = 9.21 (bs, 1H), 8.13 (bs, 1H), 7.73 (d, J = 8.32 Hz, 1H), 7.63 (d, J = 8.52 Hz, 1H), 7.27 (d, J = 8.56 Hz, 1H), 6.77 (d, J = 8.36 Hz, 1H), 3.74 (bs, 4H), 3.55-3.56 (m, 6H), 2.96-2.99 (m, 1H), 2.68-2.85 (m, 4H), 1.09-1.10 (m, 6H).<br>3. 450.2<br>4. Example 5 |
| 9 | | | | 1. 64%<br>2. ¹H-NMR (400 MHz, DMSO-d₆) δ = 8.97 (s, 1H), 8.12 (d, 1H), 7.71-7.55 (m, 2H), 7.48 (dd, 1H), 6.62 (d, 1H), 3.75 (t, 4H), 3.65 (s, 3H), 3.54 (t, 4H), 3.09-2.88 (m, 2H), 2.88-2.60 (m, 9H), 2.42-2.27 (m, 1H), 2.01 1.81 (m, 1H).<br>3. 463.28<br>4. Example 3 |

TABLE 2-continued

| Ex-amples | Halogen derivative | Amine | Product Examples | 1. Yield<br>2. ¹H-NMR<br>3. MH⁺ (ESI)<br>4. Synthesis procedure |
|---|---|---|---|---|
| 10 | (structure) | (structure) | (structure) | 1. 19%<br>2. ¹H-NMR (400 MHz, DMSO-d₆) δ = 8.88 (s, 1H), 8.47 (d, 1H), 7.59 (d, 1H), 7.48 (dd, 1H), 7.39 (d, 1H), 6.53 (dd, 1H), 3.73 (d, 4H), 3.60 (s, 3H), 3.49 (t, 4H), 2.96-2.62 (m, 4H), 2.37 (s, 7H), 2.23-2.10 (m, 1H), 1.82-1.62 (m, 1H).<br>3. 463.18<br>4. Example 4 |
| 11 | (structure) | (structure) | (structure) | 1. 50%<br>2. ¹H-NMR (400 MHz, DMSO-d₆) δ = 8.99 (s, 1H), 8.12 (s, 1H), 7.63 (dd, 2H), 7.48 (d, 1H), 6.63 (d, 1H), 3.75 (t, 4H), 3.66 (s, 3H), 3.54 (t, 4H), 3.18-2.92 (m, 2H), 2.83 (s, 9H), 2.46-2.31 (m, 1H), 1.95 (tt, 1H).<br>3. 463.30<br>4. Example 4 |
| 12 | (structure) | (structure) | (structure) | 1. 70%<br>2. ¹H-NMR (400 MHz, DMSO-d₆): δ = 1.60-1.70 (m, 1H), 2.06-2.12 (m, 1H), 2.26 (s, 6H), 2.43-2.46 (m, 1H), 2.55-2.88 (m, 5H), 3.46-3.51 (m, 4H), 3.60 (s, 3H), 3.70-3.76 (m, 4H), 6.52 (d, 1H), 7.39 (d, 1H), 7.47 (dd, 1H), 7.58 (d, 1H), 8.48 |

TABLE 2-continued

| Examples | Halogen derivative | Amine | Product Examples | 1. Yield 2. ¹H-NMR 3. MH⁺ (ESI) 4. Synthesis procedure |
|---|---|---|---|---|
| | | | | (d, 1H), 8.86 (s, 1H) 3. 463.62 4. Example 2 |
| 13 | [structure: dimethylamino-tetrahydro-pyrido-indole with Br] | [structure: 2-morpholino-benzothiazol-6-amine] | [structure: coupled product] | 1. 19% 2. ¹H-NMR (400 MHz, DMSO-d₆) δ = 8.89 (s, 1H), 8.50 (d, 1H), 7.61 (d, 1H), 7.50 (dd, 1H), 7.41 (d, 1H), 6.54 (d, 1H), 3.75 (t, 4H), 3.61 (s, 3H), 3.51 (t, 4H), 2.91-2.57 (m, 5H), 2.30 (s, 6H), 2.14 (s, 1H), 1.67 (qd, 1H). 3. 463.29 4. Example 4 |
| 14 | [structure: dimethylamino-tetrahydro-pyrido-indole with Br] | [structure: 2-(4-fluoropiperidin-1-yl)-benzothiazol-6-amine] | [structure: coupled product] | 1. 22% 2. ¹H-NMR (400 MHz, DMSO-d₆) δ = 8.89 (s, 1H), 8.48 (d, 1H), 7.61 (d, 1H), 7.54-7.42 (m, 1H), 7.40 (s, 0H), 6.55 (d, 1H), 5.11-4.79 (m, 1H), 3.86-3.50 (m, 9H), 3.02-2.65 (m, 4H), 2.45 (s, 6H), 2.17 (s, 1H), 2.12-1.93 (m, 2H), 1.93-1.69 (m, 2H). 3. 478.63 4. Example 3 |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 15 | | | | 1. 36%<br>2. ¹H-NMR (400 MHz, DMSO-d₆) δ = 8.88 (s, 1H), 8.04 (d, 1H), 7.60 (dd, 2H), 7.46 (dd, 1H), 6.59 (d, 1H), 5.04-4.72 (m, 1H), 3.93 (td, 1H), 3.84-3.53 (m, 4H), 3.53-3.06 (m, 6H), 3.04-2.66 (m, 3H), 2.41 (s, 5H), 2.27-2.05 (m, 1H), 2.05-1.58 (m, 4H).<br>3. 479.30<br>4. Example 3 |
| 16 | | | | 1. 25%<br>2. ¹H-NMR (400 MHz, DMSO-d₆) δ = 8.87 (s, 1H), 8.04 (d, 1H), 7.60 (dd, 2H), 7.46 (dd, 1H), 6.58 (d, 1H), 4.90 (dt, 1H), 4.01-3.83 (m, 1H), 3.83-3.57 (m, 6H), 3.02-2.58 (m, 5H), 2.31 (s, 6H), 2.23-2.04 (m, 1H), 2.03-1.77 (m, 3H), 1.77-1.60 (m, 2H).<br>3. 479.53<br>4. Example 3 |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 17 | | | | 1. 69%<br>2. ¹H-NMR (400 MHz, DMSO-d₆) δ = 8.90 (s, 1H), 8.36-8.18 (m, 1H), 7.59 (d, J = 8.3 Hz, 1H), 7.29 (dd, J = 8.5, 1.7 Hz, 1H), 7.20 (d, J = 8.5 Hz, 1H), 6.52 (d, J = 8.4 Hz, 1H), 3.78-3.68 (m, 4H), 3.61 (s, 3H), 3.59-3.50 (m, 4H), 2.91-2.55 (m, 5H), 2.28 (s, 6H), 2.19-2.04 (m, 1H), 1.66 (tq, J = 12.3, 6.2 Hz, 1H).<br>3. 447.09<br>4. Example 3 |
| 18 | | | | 1. 81%<br>2. ¹H-NMR (400 MHz, DMSO-d₆) δ = 8.79 (s, 1H), 7.98 (s, 1H), 7.58 (d, J = 8.3 Hz, 1H), 7.28 (s, 2H), 6.52 (d, J = 8.4 Hz, 1H), 3.76-3.68 (m, 4H), 3.60 (s, 3H), 3.59-3.53 (m, 4H), 2.90-2.79 (m, 1H), 2.79-2.56 (m, 4H), 2.28 (s, 6H), 2.17-2.04 (m, 1H), 1.66 (tq, J = 12.4, 5.9 Hz, 1H).<br>3. NA<br>4. Example 3 |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 19 | (6-chloro-2-(3-fluoropiperidin-1-yl)benzoxazole) | (N,N,9-trimethyl-2,3,4,9-tetrahydro-1H-carbazol-3-amine with pyridine fused) | (coupled product) | 1. 68.7%<br>2. ¹H-NMR (400 MHz, DMSO-d₆) δ = 8.87 (s, 1H), 8.26 (d, J = 2.0 Hz, 1H), 7.59 (d, J = 8.3 Hz, 1H), 7.29 (dd, J = 8.5, 2.1 Hz, 1H), 7.17 (d, J = 8.4 Hz, 1H), 6.52 (d, J = 8.4 Hz, 1H), 5.04-4.70 (m, 1H), 4.06-3.89 (m, 1H), 3.90-3.80 (m, 1H), 3.72-3.48 (m, 4H), 3.47-3.17 (m, 4H), 2.90-2.55 (m, 4H), 2.29 (s, 6H), 2.25-2.04 (m, 1H), 2.04-1.78 (m, 2H), 1.78-1.54 (m, 2H).<br>3. NA<br>4. Example 4 |
| 20 | (2-bromo dibenzofuran-pyridine with dimethylamino tetrahydro) | (6-amino-2-morpholinobenzothiazole) | (coupled product) | 1. 15%<br>2. ¹H-NMR (400 MHz, DMSO-d₆) δ = 9.18 (bs, 1H), 8.31 (bs, 1H), 7.72 (d, J = 8.28 Hz, 1H), 7.40-7.42 (m, 2H), 6.74 (d, J = 8.32 Hz, 1H), 3.76 (m, 4H), 3.50-3.52 (m, 4H), 2.68-2.77 (m, 5H), 2.29 (s, 6H), 2.07-2.10 (m, 1H), 1.71-1.75 (m, 1H).<br>3. 450.2<br>4. Example 5 |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 21 | | | | 1. 20%;<br>2. ¹H-NMR (400 MHz, DMSO-d₆) δ = 9.19 (bs, 1H), 8.31 (s, 1H), 7.72 (d, J = 8.00 Hz, 1H), 7.41 (s, 2H), 6.74 (d, J = 8.00 Hz, 1H), 3.74 (bs, 4H), 3.51 (bs, 4H), 2.68-2.73 (m, 4H), 2.38 (bs, 7H), 2.11-2.14 (m, 1H), 1.77 (bs, 1H).<br>3. 450.2<br>4. Example 5 |
| 22 | | | | 1. 22%;<br>2. ¹H-NMR (400 MHz, DMSO-d₆) δ = 9.19 (s, 1H), 8.31 (s, 1H), 7.72 (d, J = 8.00 Hz, 1H), 7.41 (s, 2H), 6.74 (d, J = 8.40 Hz, 1H), 3.73-3.74 (m, 4H), 3.50-3.51 (m, 4H), 2.68-2.73 (m, 5H), 2.38 (m, 6H), 2.11 (bs, 1H), 1.78 (bs, 1H)<br>3. 450.2<br>4. Example 5 |
| 23 | | | | 1. 22%<br>2. ¹H-NMR (400 MHz, DMSO-d₆) δ = 9.04 (bs, 1H), 7.73 (d, J = 1.60 Hz, 1H), 7.70 (d, J = 8.40 Hz, 1H), 7.28 (d, J = 8.40 Hz, 1H), 7.19 (dd, J = 2.00, 8.80 Hz, 1H), 6.71 (d, J = 8.40 Hz, 1H), 4.82-4.93 (m, 1H), 3.87- |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 24 | | | | 4.00 (m, 2H), 3.51-3.67 (m, 1H), 3.32-3.40 (m, 1H), 2.67-2.75 (m, 5H), 2.27 (s, 6H), 1.59-2.09 (m, 6H).<br>3. 450.2<br>4. Example 5<br>1. 18%<br>2. ¹H-NMR (400 MHz, DMSO-d₆) δ = 9.04 (bs, 1H), 7.73 (d, J = 2.00 Hz, 1H), 7.70 (d, J = 8.40 Hz, 1H), 7.28 (d, J = 8.80 Hz, 1H), 7.19 (dd, J = 2.00, 8.40 Hz, 1H), 6.71 (d, J = 8.40 Hz, 1H), 4.82-4.93 (m, 1H), 3.87-4.00 (m, 2H), 3.57-3.67 (m, 1H), 3.37-3.40 (m, 1H), 2.67-2.75 (m, 5H), 2.28 (s, 6H), 1.61-2.09 (m, 6H).<br>3. 450.2<br>4. Example 5 |
| 25 | | | | 1. 15%<br>2. ¹H-NMR (400 MHz, DMSO-d₆) δ = 9.18 (bs, 1H), 8.10 (bs, 1H), 7.71 (d, J = 8.32 Hz, 1H), 7.19 (bs, 2H), 6.72 (d, J = 8.36 Hz, 1H), 4.82-4.94 (m, 1H), 3.85-4.02 (m, 2H), 3.57-3.68 (m, 1H), 3.37-3.34 (m, 1H), 2.68-2.77 (m, 5H), 2.28 (s, 6H), 1.59-2.10 (m, 6H). |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 26 | (dimethylamino-tetrahydrobenzofuro[pyridine]-Br) | (benzoxazol-2-yl-(3-fluoropiperidin-1-yl))-aminobenzene | coupled product | 1. 10%<br>2. ¹H-NMR (400 MHz, DMSO-d₆) δ = 9.18 (bs, 1H), 8.10 (bs, 1H), 7.71 (d, J = 8.32 Hz, 1H), 7.19 (bs, 2H), 6.72 (d, J = 8.36 Hz, 1H), 4.82-4.94 (m, 1H), 3.85-4.02 (m, 2H), 3.57-3.68 (m, 1H), 3.37-3.34 (m, 1H), 2.68-2.77 (m, 5H), 2.28 (s, 6H), 1.59-2.10 (m, 6H).<br>3. 450.2<br>4. Example 50 |
| 27 | (dimethylamino-tetrahydro-carboline-Br) | (benzothiazol-2-yl-morpholino)-aminobenzene | coupled product | 1. 21%<br>2. ¹H-NMR (400 MHz, DMSO-d₆) δ = 10.81 (s, 1H), 8.81 (s, 1H), 8.48 (d, J = 1.60 Hz, 1H), 7.56 (d, J = 8.40 Hz, 1H), 7.36-7.42 (m, 2H), 6.51 (d, J = 8.40 Hz, 1H), 3.73-3.75 (m, 4H), 3.48-3.50 (m, 4H), 2.61-2.75 (m, 5H), 2.50 (s, 6H), 2.04-2.28 (m, 1H), 1.63-1.64 (m, 1H).<br>3. 449.8<br>4. Example 5 |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 28 | | | | 1. 18%<br>2. ¹H-NMR (400 MHz DMSO-d₆) δ = 9.21 (bs, 1H), 8.12 (bs, 1H), 7.72 (d, J = 8.00 Hz, 1H), 7.22 (bs, 2H), 6.73 (d, J = 8.40 Hz, 1H), 3.72-3.74 (m, 4H), 3.56-3.58 (m, 4H), 2.80-2.92 (m, 5H), 2.41 (s, 6H), 2.17 (bs, 1H), 1.84 (bs, 1H).<br>3. 434.3<br>4. Example 5 |
| 29 | | | | 1. 19%<br>2. ¹H-NMR (400 MHz, DMSO-d₆) δ = 10.89 (s, 1H), 8.24 (d, J = 2.00 Hz, 1H), 7.56-7.59 (m, 2H), 7.25-7.28 (m, 1H), 6.54 (d, J = 8.40 Hz, 1H), 3.73-3.75 (m, 4H), 3.51-3.53 (m, 4H), 2.67-2.72 (m, 5H), 2.45 (s, 6H), 2.30-2.34 (m, 1H), 1.70-1.91 (m, 1H).<br>3. 449.0<br>4. Example 5 |
| 30 | | | | 1. 22%<br>2. ¹H-NMR (400 MHz DMSO-d₆) δ = 10.89 (bs, 1H), 8.74 (bs, 1H), 8.04 (d, J = 2.00 Hz, 1H), 7.56 (d, J = 8.32 Hz, 1H), 7.25-7.27 (m, 1H), 7.18 (dd, J = 2.12, 8.66 Hz, 1H), 6.51 (d, J = 8.40 Hz, 1H), |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 31 | (structure: 2-bromo-benzofuro[3,2-b]pyridine with dimethylamino-tetrahydro substituent) | (structure: 5-amino-2-morpholinobenzoxazole) | (structure: coupled product) | 3.73 (bs, 4H), 3.52-3.58 (m, 6H), 2.68-2.84 (m, 4H), 2.34 (bs, 5H), 2.11-2.13 (m, 1H), 1.71-1.72 (m, 1H).<br>3. 433.2<br>4. Example 5<br><br>1. 16%<br>2. ¹H-NMR (400 MHz DMSO-d₆) δ = 9.09 (s, 1H), 7.78 (d, J = 2.04 Hz, 1H), 7.71 (d, J = 8.32 Hz, 1H), 7.31 (d, J = 8.64 Hz, 1H), 7.22 (dd, J = 2.16, 8.66 Hz, 1H), 6.72 (d, J = 8.40 Hz, 1H), 3.72-3.74 (m, 4H), 3.57-3.60 (m, 4H), 2.68-2.76 (m, 3H), 2.53-2.50 (m, 2H), 2.29 (s, 6H), 2.07-2.10 (m, 1H), 1.71-1.75 (m, 1H).<br>3. 434.0<br>4. Example 5 |
| 32 | (structure: 2-bromo-tetrahydro-carbazolopyridine with dimethylamino substituent) | (structure: 5-amino-2-morpholinobenzoxazole) | (structure: coupled product) | 1. 27%<br>2. ¹H-NMR (400 MHz, DMSO-d₆) δ = 10.99 (bs, 1H), 8.88 (s, 1H), 8.31 (d, J = 1.20 Hz, 1H), 7.58 (d, J = 8.40 Hz, 1H), 7.18-7.23 (m, 2H), 6.53 (d, J = 8.40 Hz, 1H), 3.72-3.75 (m, 4H), 3.53-3.55 (m, 4H), 2.67-3.33 (m, 8H), 2.50-2.51 (m, 3H), 2.26 (bs, 1H), 1.91 (bs, 1H). |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 33 | (6-bromo-tetrahydrobenzofuropyridine with N,N-dimethylamine) | (6-aminobenzothiazole with morpholine) | (coupled product) | 3. 433.2<br>4. Example 5<br>1. 12%<br>2. ¹H-NMR (400 MHz, DMSO-d₆) δ = 9.20 (s, 1H), 8.12 (d, J = 1.88 Hz, 1H), 7.74 (d, J = 8.28 Hz, 1H), 7.62 (d, J = 8.56 Hz, 1H), 7.25-7.27 (m, 1H), 6.76 (d, J = 8.32 Hz, 1H), 3.73-3.74 (m, 4H), 3.53-3.54 (m, 4H), 2.68-2.77 (m, 5H), 2.34 (s, 6H), 2.07-2.10 (m, 1H), 1.73 (bs, 1H).<br>3. 450.3<br>4. Example 5 |
| 34 | (6-bromo-tetrahydrobenzofuropyridine with N,N-dimethylamine) | (6-aminobenzothiazole with morpholine) | (coupled product) | 1. 11%<br>2. ¹H-NMR (400 MHz, DMSO-d₆) δ = 9.19 (s, 1H), 8.13 (d, J = 1.76 Hz, 1H), 7.74 (d, J = 8.32 Hz, 1H), 7.63 (d, J = 8.56 Hz, 1H), 7.25 (d, J = 1.92 Hz, 1H), 6.76 (d, J = 8.36 Hz, 1H), 3.73-3.74 (m, 4H), 3.67-3.69 (m, 4H), 2.98-3.00 (m, 2H), 2.68-2.71 (m, 3H), 2.29 (s, 6H), 2.07-2.10 (m, 1H), 1.69-1.71 (m, 1H).<br>3. 450.2<br>4. Example 5 |

TABLE 2-continued

| Examples | Halogen derivative | Amine | Product Examples | 1. Yield<br>2. ¹H-NMR<br>3. MH⁺ (ESI)<br>4. Synthesis procedure |
|---|---|---|---|---|
| 35 | | | | 1. 13%<br>2. ¹H-NMR (400 MHz, DMSO-d₆) δ = 9.09 (s, 1H), 7.78 (d, J = 2.00 Hz, 1H), 7.71 (d, J = 8.32 Hz, 1H), 7.31 (d, J = 8.64 Hz, 1H), 6.72 (d, J = 8.36 Hz, 1H), 3.72-3.73 (m, 4H), 3.55-3.57 (m, 4H), 2.67-2.68 (m, 5H), 2.33 (s, 6H), 2.08-2.11 (m, 1H), 1.74 (bs, 1H).<br>3. 434.2<br>4. Example 5 |
| 36 | | | | 1. 11%<br>2. ¹H-NMR (400 MHz, DMSO-d₆) δ = 9.06 (s, 1H), 7.76 (d, J = 1.80 Hz, 1H), 7.70 (d, J = 8.32 Hz, 1H), 7.30 (d, J = 8.60 Hz, 1H), 6.71 (d, J = 8.36 Hz, 1H), 3.71-3.72 (m, 4H), 3.56-3.57 (m, 4H), 2.67-2.69 (m, 5H), 2.27 (s, 6H), 2.06-2.08 (m, 1H), 1.69-1.71 (m, 1H).<br>3. 434.3<br>4. Example 5 |

Biological Assay Description
Full-Length Tau (flTau) Disaggregation Assay by Thioflavin T (ThT)

The longest isoform of human Tau (2N4R; 441 amino acids) was expressed in bacteria and purified. For the Tau disaggregation assay by ThT, 35 µM of recombinant full-length (fl)Tau in PBS were aggregated for 24 hours at 37° C. in presence of 50 µM of heparin (Sigma-Aldrich) and 10 mM of DTT (Sigma-Aldrich) under shaking at 750 RPM. Compounds were dissolved in anhydrous dimethyl sulfoxide (DMSO, Sigma-Aldrich) to reach a concentration of 10 mM.

flTau aggregates and serial dilutions of compounds were mixed together in PBS (volume 50 µL) to a final concentration of 2 µM of flTau aggregates and from 160 to 0.04 µM of compounds. The mixture was incubated for 30 minutes at room temperature (RT), then 40 µL of this mixture were transferred into a black 384-well plate assay (Perkin-Elmer) and mixed with 10 µL of 100 µM ThT in 250 mM glycine (both from Sigma-Aldrich) in PBS. Fluorescence (relative fluorescence units; RFU) was measured in monoplicate or duplicate on a Tecan reader (excitation: 440 nm; emission: 485 nm). Percentage of flTau disaggregation was then calculated and the halfmaximal effective concentration ($EC_{50}$) was determined using GraphPad Prism version 5 (GraphPad Software) assuming a one-binding site fitting model.

Tau K18 Disaggregation Assay by ThT

The Tau K18 fragment, encompassing amino acids 244 to 372 of the longest isoform (2N4R) of human Tau441, was expressed in bacteria and purified or bought from Signal-Chem. For the K18 disaggregation assay by ThT, 35 µM of recombinant K18 in PBS were aggregated for 24 hours at 37° C. in presence of 50 µM of heparin (Sigma-Aldrich) and 10 mM of DTT (Sigma-Aldrich) under shaking at 750 RPM. Compounds were dissolved in anhydrous dimethyl sulfoxide (DMSO, Sigma-Aldrich) to reach a concentration of 10 mM. K18 aggregates and serial dilutions of compounds were mixed together in PBS (volume 50 µL) to a final concentration of 2 µM of K18 aggregates and from 160 to 0.04 µM of compounds. The mixture was incubated for 30 minutes at room temperature (RT), then 40 µL of this mixture were transferred into a black 384-well plate assay (Perkin-Elmer) and mixed with 10 µL of 100 µM ThT in 250 mM glycine (both from Sigma-Aldrich) in PBS. Fluorescence (relative fluorescence units; RFU) was measured in monoplicate or duplicate on a Tecan reader (excitation: 440 nm; emission: 485 nm). Percentage of K18 disaggregation was then calculated and half maximal effective concentration ($EC_{50}$) was determined using GraphPad Prism version 5 (GraphPad Software) assuming a one-binding site fitting model.

The following example compounds were measured:

TABLE 3

| Example | flTau disaggregation $EC_{50}$ (µM) | TauK18 disaggregation $EC_{50}$ (µM) |
| --- | --- | --- |
| 1 | +++ | ++ |
| 2 | +++ | +++ |
| 3 | +++ | +++ |
| 5 |  | +++ |
| 6 | +++ | +++ |
| 7 |  | +++ |
| 8 |  | + |
| 9 |  | +++ |
| 10 | +++ | +++ |
| 11 | +++ | +++ |
| 12 | +++ | +++ |
| 13 | +++ | +++ |
| 14 | ++ | ++ |

TABLE 3-continued

| Example | flTau disaggregation $EC_{50}$ (µM) | TauK18 disaggregation $EC_{50}$ (µM) |
| --- | --- | --- |
| 15 | +++ | +++ |
| 16 | +++ | +++ |
| 17 | + |  |
| 18 | + | ++ |
| 19 | ++ | ++ |
| 20 |  | + |
| 21 |  | ++ |
| 22 |  | + |
| 28 |  | ++ |
| 29 | +++ |  |
| 30 | +++ |  |
| 31 | +++ | ++ |
| 32 | ++ |  |
| 33 |  | +++ |
| 34 |  | +++ |
| 35 |  | +++ |
| 36 |  | ++ |

Legend:
+++ $EC_{50}$ < 10 uM;
++ $EC_{50}$ 10 < x < 25 uM;
+ $EC_{50}$ 25 < x < 50 uM.

Reduction of Intracellular Tau Aggregation

A human neuroblastoma cell line overexpressing the full-length form of human Tau carrying the P301L mutation was cultured in complete medium [DMEM-F12 4.5 g/L Glutamax (Invitrogen), 15% FBS (Biochrom), 1% Peni/Strep (Invitrogen) supplemented with 2.5 µg/ml of G418 (Sigma-Aldrich) selection antibiotic]. The day before the experiment $5 \times 10^5$ cells/well were plated in a 6 well plate in 3 mL of complete medium. The next day, cells were incubated with DMSO or a compound of the present invention at a 5 µM for additional 24 h at 37° C. After incubation, cells were trypsinized, resuspended in 100 µl of homogenization buffer [25 mM Tris-HCl pH 7.4, 150 mM NaCl, 1 mM EDTA, 1 mM EGTA containing phosphatase inhibitors (30 mM NaF, 0.2 mM $Na_3VO_4$, 1 nM Okadaic acid, 1 mM PMSF, 5 mM $Na_4P_2O_7$) and protease inhibitor cocktail (Complete™, Roche)], and then physically lysed with three rapid cycles of freezing and thawing. Samples were then directly tested in the AlphaLISA assay.

Phosphorylated, aggregated, and total Tau were quantified by AlphaLisa using the following antibody pairs:
HT7-Acceptor beads+biotin (BT)-Tau13-Donor beads: Total Tau
HT7-Acceptor beads+biotin (BT)-HT7-Donor beads: Aggregated human Tau The Tau13 (Abcam) was biotinylated using EZ-Link® NHS-PEO Solid Phase biotinylation kit (Thermo Scientific), while the HT7-biotin was from a commercial source (Thermo Scientific).

For each antibody pairs the concentration of acceptor beads and biotinylated antibodies was optimized. All samples were first tested in a dilution series in PBS in order to identify the linear range and optimal dilution for each sample and assay. For the final protocol, the following reagents were added in a 384-well white OptiPlate (Perkin Elmer):
5 µL of test diluted sample
20 µL of the mixture biotin-mAb acceptor beads at the following final concentrations:
HT7-BT at 1.25 nM in combination with HT7-Acc beads at 10 µg/ml
Tau13-BT at 5 nM in combination with HT7-Acc beads at 2.5 µg/ml After incubation of this mixture at room temperature for 1 h, 25 μL of Streptavidin Donor beads (Perkin Elmer) at 25 μg/mL were added in the dark. Plates were analyzed after 30 min incubation using the EnSpire Alpha instrument and EnSpire Workstation version 3.00.

Data for aggregated Tau were normalized to total Tau and then expressed as percentage of the DMSO-treated cells.

The following example compounds were measured:

TABLE 4

| Example | % Reduction of intracellular Tau aggregation |
|---|---|
| 1 | + |
| 2 | + |
| 3 | ++ |
| 12 | ++ |

Legend:
+++ % > 50;
++ %50 < x < 25;
+ %25 < x < 10.

In Vivo Efficacy of the Compounds of the Present Invention
In Vivo Study Design for the Testing of Example 1 and Example 12

Double transgenic rTg4510 mice are an aggressive Tauopathy model expressing the full-length human Tau carrying the P301L mutation (Tau4R0N-P301L) under the control of the tetracycline-inducible CaMKII promoter (Ramsden et al., J. Neurosci., 2005•25(46):10637-10647). Wild-type animals and single transgenic mice expressing only the tetracycline-controlled transactivator (tTA) were used as genotype controls. The study comprised 6 treatment groups (n=20 mice/group) with the following group distribution (see Table 5). Compounds or vehicle control were administered once daily by gavage for 12.5 weeks starting at the age of 5.5 weeks. The Morris Water Maze (MWM) behavioral test was performed after 12.5 weeks of treatment over 5 consecutive days. During MWM testing daily dosing was continued. Behavioral testing (MWM) was performed only on female mice (around n=11 female/group). Measurements of cortical atrophy and histology for misfolded Tau (MC1) and CD68 were performed on 7 animals/group excluding wild-type animals.

TABLE 5

In vivo study design for the testing of Example 1 and Example 12

| Genotype | Number of mice | Treatment/dose |
|---|---|---|
| Wild-type | 20 | Vehicle[a] |
| tTA | 20 | Vehicle[a] |
| rTg4510 | 20 | Vehicle[a] |
| rTg4510 | 20 | Example 1 (7 mg/kg) |
| rTg4510 | 20 | Example 1 (20 mg/kg) |
| rTg4510 | 20 | Example 12 (20 mg/kg) |

(a) Vehicle: 0.5% w/v Hydroxypropylmethylcellulose 4000 cps; 0.5% w/v Tween 80

Morris Water Maze (MWM) Behavioral Test on rTg4510 Mice Treated with the Compounds of Invention The MWM was performed in a circular tank, measuring 48" in diameter. The water was approximately 24-25" deep, and colored white with non-toxic paint. The water was maintained at 25° C.±1° C. Extra-maze cues were mounted around the water tank. Trials were video recorded and analyzed by a computer program (WaterMaze; Actimetrics, Wilmette, Ill.). On 5 consecutive days of the first week, training sessions were conducted with the platform submerged approximately 1.5 cm below the surface of the water. On each day, there were four 60-s long trials, with a 15-min inter-trial interval, approximately. On the fifth day of training, the last fourth trial consisted of 60 s without the platform (probe trial). The platform position and release points were counterbalanced across treatment groups. Percent time spent in each quadrant (target, left and right adjacent, and opposite) were calculated for probe trials. Data corresponding to the adjacent quadrants were averaged. Data were analyzed by 2-way ANOVA followed by post-hoc comparisons and shown statistics refers to differences compared to vehicle treated rTg4510 mice.

As shown in FIG. 1, the compound of invention, Example 1, showed a dose-dependent increase in the percentage of time spent in the target quadrant. Another compound of the invention, Example 12, also showed a significant increase in the percentage of time spent in the target quadrant. These data indicate that treatment with both compounds tested in rTg4510 significantly improved the memory performance of this aggressive Tau transgenic model.

Histological Evaluation of rTg4510 Mice Treated with Example 1 and Example 12

After behavioral testing, mice were deeply anesthetized by standard injectable anesthesia and transcardially perfused with cold PBS. Brains were then removed and hemi-sagitally hemisected. The left hemispheres were snap frozen in dry ice and stored at −80° C., before being used for biochemical analysis. The right hemispheres were fixed in 4% paraformaldehyde in PBS for three hours at room temperature, cryopreserved by immersion in 15% sucrose at 4° C. for three days, and prepared for cryosectioning. Fixed hemispheres were then frozen in dry ice on OCT medium in cryo molds and sagittally cryosectioned (10 μm thickness) with Leica CM3050S cryotome. Sections from 7 mice per group, excluding wild-type animals, were collected from around 10 mediolateral levels starting 0.2 mm lateral from midline, mounted on slides, and used to quantify the cortex size. Sections from level 4 were used for MC1 histological staining. Briefly, sections were encircled with pap pen liquid blocker and washed three times 5 minutes in PBS. Blocking and permeabilization were performed for 2 hours at room temperature with 10% neat goat serum (NGS) and 0.25% Triton X-100 in PBS. Sections were then paper blotted and incubated with mouse monoclonal MC-1 antibody diluted 1:1000 in PBS with 5% NGS and 0.25% Triton-X 100 overnight at 4° C. in a humid chamber. Following three 5 minutes washes in PBS, sections were incubated with the goat anti-mouse IgG AlexaFluo 555 (Invitrogen) secondary antibodies at 1:1000 in PBS for 30 minutes at room temperature and subsequently washed three times 5 minutes in PBS. To reduce auto-fluorescence of the tissue, sections were incubated with a solution of 0.1% Sudan Black (Sigma) in 70% ethanol for 15 minutes at room temperature, then washed four times 5 minutes in PBS, and mounted using ProLong Gold Antifade reagent (Invitrogen). Staining was visualized on the Nikon Eclipse Ti microscope, imaged using Nikon DS-Fi2 camera, and quantified using the NIS-Element AR4.13.1 software. Reported values are the average of the quantification three individual pictures per sample.

A systematic random set of sections for five sagittal sections per animal (a total of 175 sections) was used for CD68 histological staining. Briefly, sections were labeled for rat anti mouse CD68 clone FA-11 (BD Biosciences) and counterstained with DAPI. Antibody binding was visualized using highly cross-absorbed fluorescently labeled secondary antibodies (Thermo Fisher). The antibody was diluted in antibody diluent (Dako), unspecific endogenous IgG binding was blocked with M.O.M. serum (Vector) before primary incubation. Mounted sections were imaged as a whole on an Axio.Scan Z1 slide scanner driven by ZEN software at 20× magnification (plan apochromatic objective), using LED (Colibri2) illumination and a sensitive Orca Flash 4.0 monochromatic camera. Data were analyzed by 1-way ANOVA followed by post-hoc comparisons and shown statistics refers to differences compared to vehicle treated rTg4510 mice.

Figure 2:
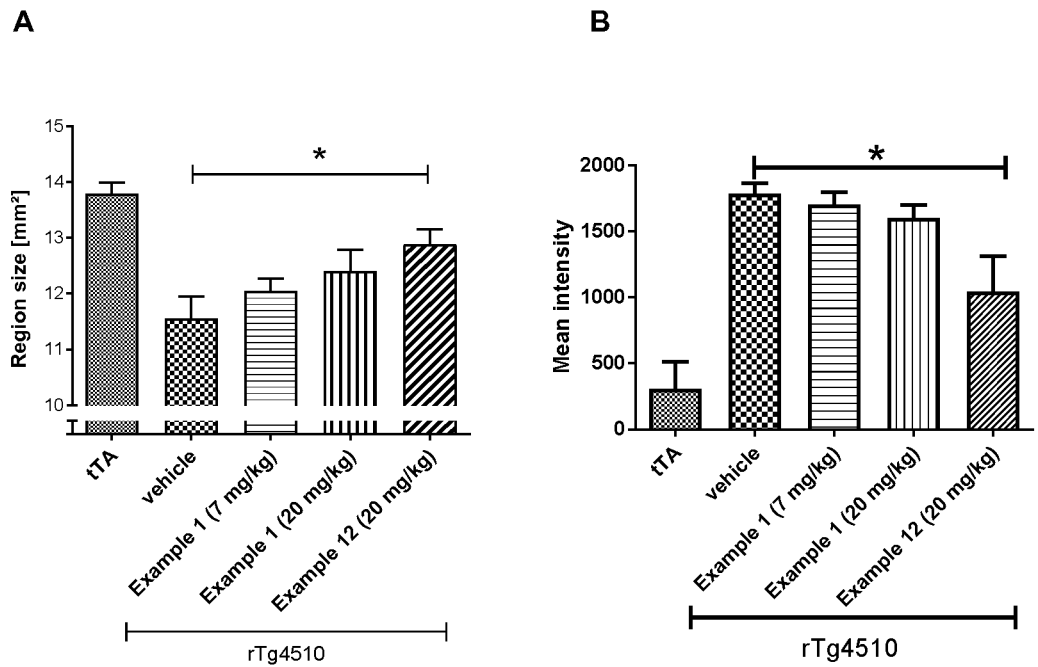
FIG. 2: Cortex atrophy (A) and Tau misfolding (B) quantification in rTg4510 mice treated with Example 1 and Example 12.

As shown in FIG. 2A, the compound of the invention, Example 1, showed a dose-dependent increase of the cortex size. Another compound of the invention, Example 12, also showed a significant increase of the cortex size. These data indicate that treatment with both compounds tested in rTg4510 ameliorated the cortical atrophy of this aggressive Tau transgenic model.

The rescue of the cortical atrophy was also complemented by a reduction of Tau misfolding, measured by MC1 histology. As shown in FIG. 2B, the compound of the invention, Example 1, showed a dose-dependent decrease of misfolded Tau. Another compound of the invention, Example 12, also showed a significant decrease of misfolded Tau. These data indicate that treatment with both compounds tested in rTg4510 decreased the levels of pathological Tau in this aggressive Tau transgenic model.

Figure 3:
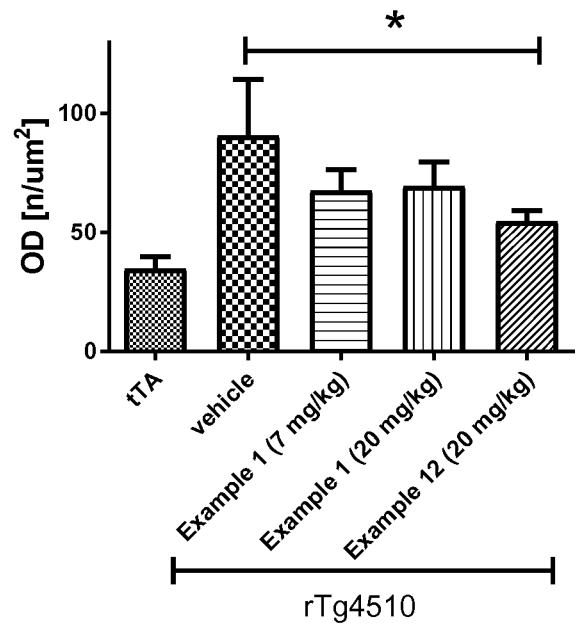
FIG. 3: CD68 quantification in rTg4510 mice treated with Example 1 and Example 12.

To assess whether the above described effect of tested compounds on Tau had also an effect on neuroinflammation markers, the effect of compounds of the invention on neuroinflammation was evaluated using the microglia phagocytosis marker CD68 that stains hyperactive microglial cells. As shown in FIG. 3, the compound of the invention, Example 1, showed a decrease in CD68 positive microglia. Another compound of the invention, Example 12, also showed a significant decrease in CD68 positive microglia. These data indicate that treatment with both compounds tested in rTg4510 decreased the levels of neuroinflammation in this aggressive Tau transgenic model.

In Vivo Study Design for the Testing of Example 2

Double transgenic rTg4510 mice are an aggressive Tauopathy model expressing the full-length human Tau carrying the P301L mutation (Tau4R0N-P301L) under the control of the tetracycline-inducible CaMKII promoter (Ramsden et al., 2005). Wild-type animals and single transgenic mice expressing only the tetracycline-controlled transactivator (tTA) were used as genotype controls. Mice were treated and tested. The study comprised 4 treatment groups (n=15 female mice/group) with the following group distribution (see Table 6). Compound of the invention or vehicle control were administered once daily by gavage for 12 weeks starting at the age of 5.5 weeks. The Morris Water Maze (MWM) behavioral test was performed after 12.5 weeks of treatment over 5 consecutive days. During MWM testing daily dosing was continued. Behavioral testing (MWM) and biochemical quantification of sarkosyl-insoluble Tau were performed on all mice (n=15 mice/group). Measurement of cortical atrophy and histology for Iba1 were performed on 10 mice/group.

TABLE 6

In vivo study design for the testing of Example 2

| Genotype | Number of mice | Treatment/dose |
|---|---|---|
| tTA | 15 | Vehicle[a] |
| rTg4510 | 15 | Vehicle[a] |
| rTg4510 | 15 | Example 2 (7 mg/kg) |
| rTg4510 | 15 | Example 2 (20 mg/kg) |

(a) Vehicle: 0.5% Hydroxypropylmethylcellulose 4000 cps; 0.5% w/v Tween 80

Morris Water Maze (MWM) Behavioral Test on rTg4510 Mice Treated with Example 2

The MWM was performed in a circular tank, measuring 48" in diameter. The water was approximately 24 to 25" deep, and colored white with non-toxic paint. The water was maintained at 25° C.±1° C. Extra-maze cues were mounted around the water tank. Trials were video recorded and analyzed by a computer program (WaterMaze; Actimetrics, Wilmette, Ill.). On 5 consecutive days of the first week, training sessions were conducted with the platform submerged approximately 1.5 cm below the surface of the water. On each day, there were four 60-s long trials, with a 15-min inter-trial interval, approximately. On the fifth day of training, the last fourth trial consisted of 60 s without the platform (probe trial). The platform position and release points were counterbalanced across treatment groups. Percent crossing in each quadrant (target, left and right adjacent, and opposite) was calculated for probe trials. Data were analyzed by 2-way ANOVA followed by post-hoc comparisons and shown statistics refers to differences compared to vehicle treated rTg4510 mice.

Figure 4:
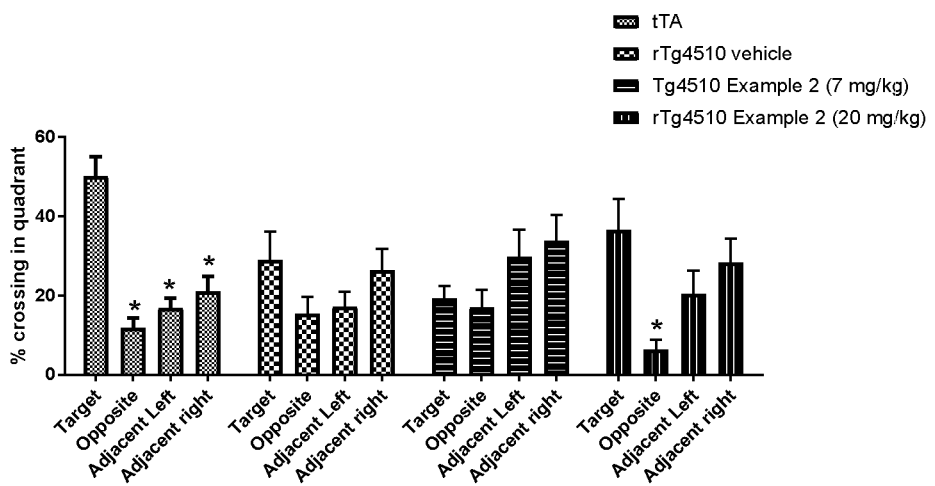
FIG. 4: Morris Water Mazer behavioral test on rTg4510 mice treated with Example 2.

As shown in FIG. 4, the compound of invention, Example 2, showed a dose-dependent increase in the percentage of platform crossings in the target compared to the opposite quadrant, reaching statistical significance at the dose of 20 mg/kg. These data indicate that treatment with the compound tested in rTg4510 significantly improves the memory performance of this aggressive Tau transgenic model.

Biochemical Evaluation of rTg4510 Mice Treated with Example 2

After behavioral testing, mice were deeply anesthetized by standard injectable anesthesia and transcardially perfused with cold PBS. Brains were then removed and hemi-sagittally hemisected. From left brain hemispheres, cortices were dissected, weighed, rapidly immersed in liquid nitrogen and stored at −80° C. until use for biochemical analysis. For the preparation of cortical total brain homogenates (Cx-TBH), frozen cortices were homogenized in 9 volumes (ml)/weight (g) of ice-cold homogenization buffer [25 mM Tris-HCl pH 7.4, 150 mM NaCl, 1 mM EDTA, 1 mM EGTA containing phosphatase inhibitors (30 mM NaF, 0.2 mM $Na_3VO_4$, 1 nM okadaic acid, 1 mM PMSF, 5 mM $Na_4P_2O_7$) supplemented with protease inhibitor cocktail (Complete™, Roche)]. Homogeinization was performed using an electric homogenizer with a 1.5 ml pestle (VWR). 150 µl of Cx-TBH was then mixed with a sucrose solution (100%) to a final sucrose concentration of 10% and centrifuged at 20'000 g for 20 minutes at 4° C. Supernatants were collected, mixed with sarcosyl (20%) to a final sarcosyl concentration of 1% and incubated under agitation for 1 hour at room temperature. Samples were then centrifuged at 100'000 g for 1 hour at 4° C. The pellet containing the sarkosyl-insoluble fraction was resuspended in 40 µl of 50 mM Tris-HCl pH7.4 and were mixed with loading buffer (LiCor) containing 10% β-mercaptoethanol, heated at 98° C. for 10 minutes and loaded into a Bolt 4-12% Bis-Tris Plus gel (Novex). Samples were run in NuPAGE MOPS SDS running buffer (Invitrogen) for 2 hours at 100V. After migration of the samples, proteins were transferred on a PVDF membrane (0.45 µm, Immobilion) for 2 hours at 100V in ice-cold transfer buffer [25 mM Tris pH8.3, 190 mM glycine, 20% ethanol]. Membranes were then blocked for 1 hour at room temperature in a 1:3 dilution of Odyssey blocking buffer (LiCor) in PBS in order to reduce unspecific binding. After blocking, membranes were incubated with a mouse anti-Tau13 (SantaCruz) at 1:1000. Subsequently, membranes were washed 3 times 15 minutes with PBS containing 0.1% Tween 20 and then incubated for 1 hour at room temperature with a goat-anti-mouse-IRDye® 800CW (LiCor) secondary antibody. Secondary antibodies were diluted 1:10000 in a 1:3 dilution of Odyssey blocking buffer (LiCor) in PBS containing 0.1% Tween 20. Subsequently, membranes were washed 3 times 15 minutes in PBS containing 0.1% Tween 20 followed by 3 washes of 5 minutes in PBS. The membranes were finally scanned using LiCor scanner (Odyssey Infrared Imager) and quantified using the LiCor software Image Studio Lite Version 5.2. Data were normalized to an internal control sample loaded in each gel.

Figure 5:
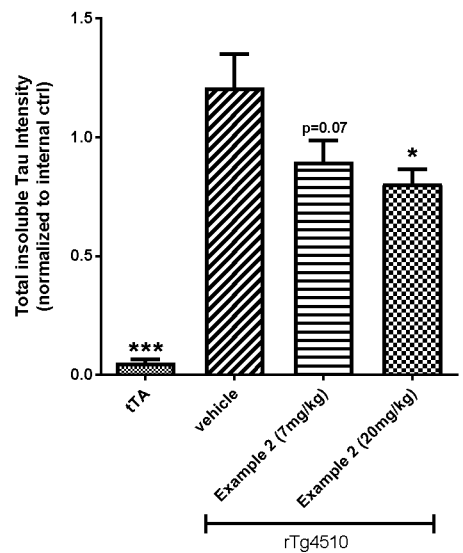
FIG. 5: Quantification of sarkosyl-insoluble Tau in rTg4510 mice treated with Example 2.

As shown in FIG. 5, the compound or invention, Example 2, showed a dose-dependent decrease of the sarkosyl insoluble Tau that reaches statistical significance at the higher dose of 20 mg/kg. These data indicate that treatment with the compound tested in rTg4510 decreases pathological Tau in this aggressive Tau transgenic model.

Histological Evaluation of rTg4510 Mice Treated with Example 2

Figure 6:
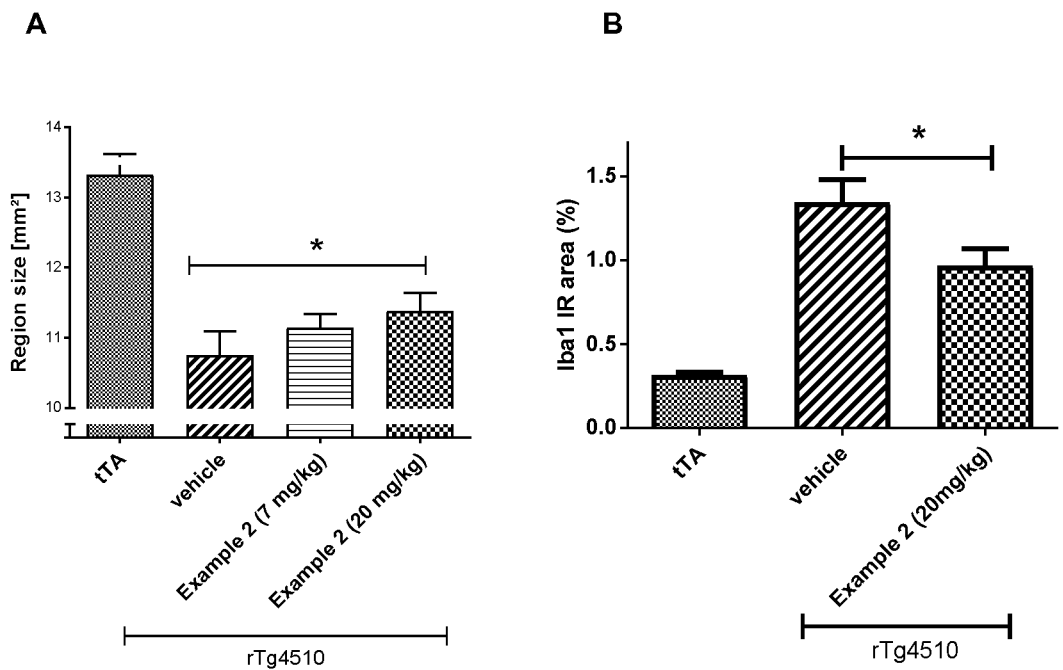
FIG. 6: Cortex atrophy (A) and Iba1 positive microglial (B) quantification in rTg4510 mice treated with Example 2.

After behavioral testing, mice were deeply anesthetized by standard injectable anesthesia and transcardially perfused with cold PBS. Brains were then removed and hemi-sagitally hemisected. The right hemispheres were fixed in 4% paraformaldehyde in PBS for three hours at room temperature, cryopreserved by immersion in 15% sucrose at 4° C. for three days, and prepared for cryosectioning. Fixed hemispheres were then frozen in dry ice on OCT medium in cryo molds and sagittally cryosectioned (10 µm thickness) with Leica CM1950 cryotome. Sections from 10 mice per group were collected from around 12 mediolateral levels. A systematic random set of sections from seven sagittal levels per animal was used to quantify the cortex size. As shown in FIG. 6A, the compound of the invention, Example 2, showed a dose-dependent increase of the cortex size that reaches statistical significance at the higher dose. These data indicate that treatment with the compound tested in rTg4510 ameliorates the cortical atrophy of this aggressive Tau transgenic model.

One section per animal from layer 6 was also used to quantify the Iba1 immunoreactivity. Briefly, cryosections were removed from −20° C. and air-dried for 25 minutes at room temperature. Brain tissue was encircled with pap pen liquid blocker and washed one time 5 minutes and one time 10 minutes in PBS at room temperature. Blocking and permeabilization were performed for 2 hours at room temperature with 10% normal goat serum (NGS) and 0.25% Triton X-100 in PBS. Sections were then paper blotted and incubated with rabbit polyclonal Iba1 antibody (Wako) diluted 1:450 in PBS containing 5% NGS and 0.25% Triton X-100 overnight at 4° C. in a humid chamber. Sections were washed three times 10 minutes in PBS at room temperature and incubated with a Cy3-labeled goat anti-rabbit IgG (H+L) secondary antibody (Jackson) diluted 1:1000 in PBS for 30 minutes at room temperature protected from light. Following three washes for 10 minutes in PBS, sections were incubated with a solution of 0.1% Sudan Black (Sigma) in 70% ethanol for 30 seconds at room temperature in order to reduce autofluorescence of the tissue. Sections were washed three times for 10 minutes in PBS, mounted using ProLong Gold Antifade reagent with DAPI (Molecular Probes) and coverslipped. Sections were imaged using a digital slide scanner (Pannoramic 250 BF Flash+FL, 3D Histech Ltd.) and quantified using the image visualization software CaseViewer and the image analysis software module HistoQuant (3D Histech Ltd.).

As shown in FIG. 6B, the compound of invention, Example 2, at 20 mg/kg showed a significant decrease in the Iba1 immunoreactive area. These data indicate that treatment with the compound tested in rTg4510 decreases microgliosis and thus neuroinflammation in this aggressive Tau transgenic model.

The invention claimed is:

1. A compound of formula (I):

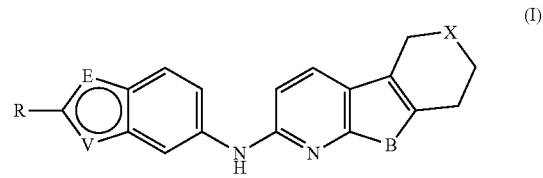

(I)

and all stereoisomers, racemic mixtures, tautomers, pharmaceutically acceptable salts, hydrates, solvates and polymorphs thereof;

wherein

B is selected from the group consisting of O and $NR^a$;

E is N and V is S, E is S and V is N, E is N and V is O, or E is O and V is N;

X is selected from the group consisting of $N-R^6$ and $HC-N(Me)_2$;

R is independently selected from the group consisting of

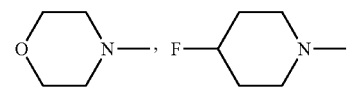

and

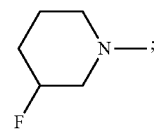

$R^a$ is selected from the group consisting of H and alkyl; and $R^6$ is alkyl.

2. The compound according to claim 1, which is a compound of formula (Ia):

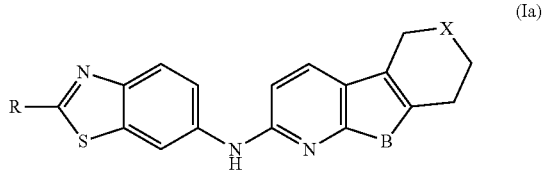

(Ia)

wherein B, R, and X are as defined in claim 1.

3. The compound according to claim 2, which is a compound of formula (Ib):

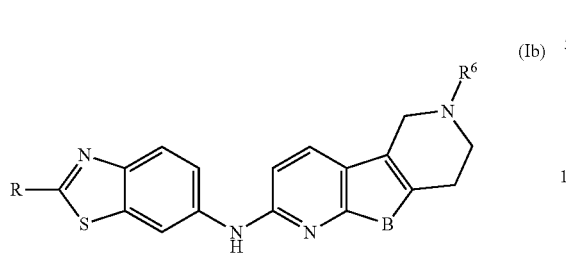
(Ib)

wherein B is selected from the group consisting of O and NR$^a$;

R is independently selected from the group consisting of

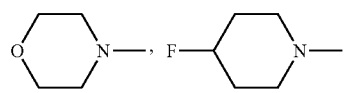

and

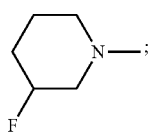

and

R$^6$ is alkyl.

4. The compound according to claim 2, which is a compound of formula (Ic):

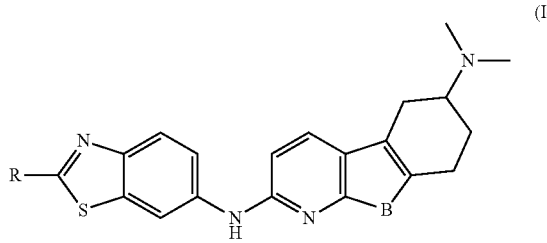
(Ic)

wherein B is selected from the group consisting of O and NR$^a$; and

R is independently selected from the group consisting of

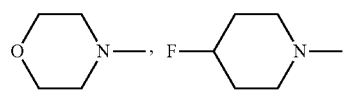

and

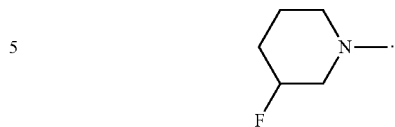

5. A pharmaceutical composition comprising a compound as defined in claim 1 and a pharmaceutically acceptable carrier or excipient.

6. A method of treating or alleviating a disorder caused by Tau protein aggregates, the method comprising administering an effective amount of a compound as defined in claim 1 to a patient in need thereof.

7. The method according to claim 6, wherein the disorder is selected from Alzheimer's disease (AD), familial AD, Primary Age-Related Tauopathy (PART), Creutzfeldt-Jacob disease, dementia pugilistica, Down's Syndrome, Gerstmann-Sträussler-Scheinker disease (GSS), inclusion-body myositis, prion protein cerebral amyloid angiopathy, Parkinsonism-dementia complex of Guam, non-Guamanian motor neuron disease with neurofibrillary tangles, argyrophilic grain disease, diffuse neurofibrillary tangles with calcification, Hallervorden-Spatz disease, multiple system atrophy (MSA), Niemann-Pick disease type C, pallido-ponto-nigral degeneration, progressive subcortical gliosis, subacute sclerosing panencephalitis, tangle predominant dementia, post-encephalitic Parkinsonism, myotonic dystrophy, subacute sclerosis panencephalopathy, mutations in LRRK2, familial British dementia, familial Danish dementia, frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease.

8. The method according to claim 7, wherein the disorder is selected from the group consisting of Alzheimer's disease (AD), corticobasal degeneration (CBD), Pick's disease (PiD), and progressive supranuclear palsy (PSP).

9. The method according to claim 7, wherein the frontotemporal lobar degeneration is selected from the group consisting of traumatic brain injury (TBI), amyotrophic lateral sclerosis (ALS), corticobasal degeneration (CBD), frontotemporal dementia with Parkinsonism linked to chromosome 17 (FTDP-17), Pick's disease (PiD), progressive supranuclear palsy (PSP), and chronic traumatic encephalopathy (CTE).

10. A mixture comprising a compound as defined in claim 1 and at least one further biologically active compound selected from a therapeutic agent different from the compound as defined in claim 1, a pharmaceutically acceptable carrier, a diluent and an excipient.

11. The mixture according to claim 10, wherein the further biologically active compound is a compound used in the treatment of amyloidosis.

12. The mixture according to claim 10, wherein the further biologically active compound is selected from the group consisting of compounds against oxidative stress, anti-apoptotic compounds, metal chelators, inhibitors of DNA repair, α-secretase activators, β- and γ-secretase inhibitors, Tau proteins, neurotransmitters, β-sheet breakers, attractants for amyloid beta clearing/depleting cellular components, inhibitors of N-terminal truncated amyloid beta, anti-inflammatory molecules, cholinesterase inhibitors (ChEIs), M1 agonists, an antibody, any functionally equivalent antibody or functional parts thereof of an antibody, and a vaccine.

13. The mixture according to claim 12,
   wherein the inhibitor of DNA repair is selected from the group consisting of pirenzepine and metabolites, 3-amino-1-propanesulfonic acid (3APS), and 1,3-propanedisulfonate (1,3PDS);
   wherein the inhibitor of N-terminal truncated amyloid beta is pyroglutamated amyloid beta 3-42; and
   wherein the cholinesterase inhibitor is selected from the group consisting of tacrine, rivastigmine, donepezil, and galantamine.

* * * * *